(12) United States Patent
Lopez Camacho et al.

(10) Patent No.: US 12,023,073 B2
(45) Date of Patent: Jul. 2, 2024

(54) ADJUSTABLE IMPLANT

(71) Applicant: Nuvasive Specialized Orthopedics, Inc., San Diego, CA (US)

(72) Inventors: Jorge Lopez Camacho, Oxnard, CA (US); Shawn Placie, Aliso Viejo, CA (US); Michael Moeller, Carlsbad, CA (US)

(73) Assignee: NUVASIVE SPECIALIZED ORTHOPEDICS, INC., San Diego, CA (US)

( * ) Notice: Subject to any disclaimer, the term of this patent is extended or adjusted under 35 U.S.C. 154(b) by 28 days.

(21) Appl. No.: 17/815,694

(22) Filed: Jul. 28, 2022

(65) Prior Publication Data
US 2023/0041121 A1 Feb. 9, 2023

Related U.S. Application Data

(60) Provisional application No. 63/229,014, filed on Aug. 3, 2021.

(51) Int. Cl.
| | | |
|---|---|---|
| A61B 17/72 | (2006.01) | |
| A61B 17/00 | (2006.01) | |
| A61B 17/68 | (2006.01) | |
| A61B 17/70 | (2006.01) | |

(52) U.S. Cl.
CPC ...... *A61B 17/7225* (2013.01); *A61B 2017/00367* (2013.01); *A61B 2017/00398* (2013.01); *A61B 2017/681* (2013.01); *A61B 17/7002* (2013.01)

(58) Field of Classification Search
CPC ............ A61B 17/7016; A61B 17/7216; A61B 17/7225; A61B 2017/681; A61B 2017/00398; A61B 2017/00402; A61B 2017/00411; A61B 2017/00876; A61B 17/7014–7017; A61B 17/66–666
See application file for complete search history.

(56) References Cited

U.S. PATENT DOCUMENTS

| | | |
|---|---|---|
| 2,702,031 A | 2/1955 | Wenger |
| 3,111,945 A | 11/1963 | Von Solbrig |
| 3,372,476 A | 3/1968 | Peiffer |
| 3,377,576 A | 4/1968 | Langberg |
| 3,512,901 A | 5/1970 | Law |

(Continued)

FOREIGN PATENT DOCUMENTS

| | | |
|---|---|---|
| CN | 1697630 A | 11/2005 |
| CN | 101040807 A | 9/2007 |

(Continued)

OTHER PUBLICATIONS

Invitation to Pay Additional Fees (with partial International Search Report), PCT/US2022/038622, dated Nov. 9, 2022, 12 pages.

(Continued)

*Primary Examiner* — Julianna N Harvey
*Assistant Examiner* — Anna V. Little

(57) ABSTRACT

One aspect of the disclosure relates to an aspect of the disclosure relates to an adjustable implant including: a housing; a first adjustable member at least partially positioned within the housing and moveable relative to the housing; and a first actuation assembly positioned within the first adjustable member and configured to move the first adjustable member relative to the housing.

17 Claims, 16 Drawing Sheets

(56) References Cited

U.S. PATENT DOCUMENTS

| | | |
|---|---|---|
| 3,597,781 A | 8/1971 | Eibes |
| 3,900,025 A | 8/1975 | Barnes, Jr. |
| 3,915,151 A | 10/1975 | Kraus |
| RE28,907 E | 7/1976 | Eibes et al. |
| 3,976,060 A | 8/1976 | Hildebrandt et al. |
| 4,010,758 A | 3/1977 | Rockland et al. |
| 4,056,743 A | 11/1977 | Clifford et al. |
| 4,068,821 A | 1/1978 | Morrison |
| 4,078,559 A | 3/1978 | Nissinen |
| 4,204,541 A | 5/1980 | Kapitanov |
| 4,357,946 A | 11/1982 | Dutcher et al. |
| 4,386,603 A | 6/1983 | Mayfield |
| 4,448,191 A | 5/1984 | Rodnyansky et al. |
| 4,486,176 A | 12/1984 | Tardieu et al. |
| 4,501,266 A | 2/1985 | McDaniel |
| 4,522,501 A | 6/1985 | Shannon |
| 4,537,520 A | 8/1985 | Ochiai et al. |
| 4,550,279 A | 10/1985 | Klein |
| 4,561,798 A | 12/1985 | Elcrin et al. |
| 4,573,454 A | 3/1986 | Hoffman |
| 4,592,355 A | 6/1986 | Antebi |
| 4,595,007 A | 6/1986 | Mericle |
| 4,642,257 A | 2/1987 | Chase |
| 4,658,809 A | 4/1987 | Ulrich et al. |
| 4,700,091 A | 10/1987 | Wuthrich |
| 4,747,832 A | 5/1988 | Buffet |
| 4,854,304 A | 8/1989 | Zielke |
| 4,904,861 A | 2/1990 | Epstein et al. |
| 4,931,055 A | 6/1990 | Bumpus et al. |
| 4,940,467 A | 7/1990 | Tronzo |
| 4,957,495 A | 9/1990 | Kluger |
| 4,973,331 A | 11/1990 | Pursley et al. |
| 5,010,879 A | 4/1991 | Moriya et al. |
| 5,030,235 A | 7/1991 | Campbell, Jr. |
| 5,041,112 A | 8/1991 | Mingozzi et al. |
| 5,064,004 A | 11/1991 | Lundell |
| 5,074,882 A | 12/1991 | Grammont et al. |
| 5,092,889 A | 3/1992 | Campbell, Jr. |
| 5,133,716 A | 7/1992 | Plaza |
| 5,142,407 A | 8/1992 | Varaprasad et al. |
| 5,156,605 A | 10/1992 | Pursley et al. |
| 5,263,955 A | 11/1993 | Baumgart et al. |
| 5,290,289 A | 3/1994 | Sanders et al. |
| 5,306,275 A | 4/1994 | Bryan |
| 5,330,503 A | 7/1994 | Yoon |
| 5,334,202 A | 8/1994 | Carter |
| 5,336,223 A | 8/1994 | Rogers |
| 5,356,411 A | 10/1994 | Spievack |
| 5,356,424 A | 10/1994 | Buzerak et al. |
| 5,364,396 A | 11/1994 | Robinson et al. |
| 5,403,322 A | 4/1995 | Herzenberg et al. |
| 5,429,638 A | 7/1995 | Muschler et al. |
| 5,437,266 A | 8/1995 | McPherson et al. |
| 5,466,261 A | 11/1995 | Richelsoph |
| 5,468,030 A | 11/1995 | Walling |
| 5,480,437 A | 1/1996 | Draenert |
| 5,509,888 A | 4/1996 | Miller |
| 5,516,335 A | 5/1996 | Kummer et al. |
| 5,527,309 A | 6/1996 | Shelton |
| 5,536,269 A | 7/1996 | Spievack |
| 5,549,610 A | 8/1996 | Russell et al. |
| 5,573,012 A | 11/1996 | McEwan |
| 5,575,790 A | 11/1996 | Chen et al. |
| 5,582,616 A | 12/1996 | Bolduc et al. |
| 5,620,445 A | 4/1997 | Brosnahan et al. |
| 5,620,449 A | 4/1997 | Faccioli et al. |
| 5,626,579 A | 5/1997 | Muschler et al. |
| 5,626,613 A | 5/1997 | Schmieding |
| 5,632,744 A | 5/1997 | Campbell, Jr. |
| 5,659,217 A | 8/1997 | Petersen |
| 5,662,683 A | 9/1997 | Kay |
| 5,672,175 A | 9/1997 | Martin |
| 5,672,177 A | 9/1997 | Seldin |
| 5,700,263 A | 12/1997 | Schendel |
| 5,704,938 A | 1/1998 | Staehlin et al. |
| 5,704,939 A | 1/1998 | Justin |
| 5,720,746 A | 2/1998 | Soubeiran |
| 5,743,910 A | 4/1998 | Bays et al. |
| 5,762,599 A | 6/1998 | Sohn |
| 5,771,903 A | 6/1998 | Jakobsson |
| 5,810,815 A | 9/1998 | Morales |
| 5,827,286 A | 10/1998 | Incavo et al. |
| 5,830,221 A | 11/1998 | Stein et al. |
| 5,879,375 A | 3/1999 | Larson, Jr. et al. |
| 5,902,304 A | 5/1999 | Walker et al. |
| 5,935,127 A | 8/1999 | Border |
| 5,945,762 A | 8/1999 | Chen et al. |
| 5,961,553 A | 10/1999 | Coty et al. |
| 5,976,138 A | 11/1999 | Baumgart et al. |
| 5,979,456 A | 11/1999 | Magovern |
| 6,022,349 A | 2/2000 | McLeod et al. |
| 6,033,412 A | 3/2000 | Losken et al. |
| 6,034,296 A | 3/2000 | Elvin et al. |
| 6,102,922 A | 8/2000 | Jakobsson et al. |
| 6,106,525 A | 8/2000 | Sachse |
| 6,126,660 A | 10/2000 | Dietz |
| 6,126,661 A | 10/2000 | Faccioli et al. |
| 6,138,681 A | 10/2000 | Chen et al. |
| 6,139,316 A | 10/2000 | Sachdeva et al. |
| 6,162,223 A | 12/2000 | Orsak et al. |
| 6,183,476 B1 | 2/2001 | Gerhardt et al. |
| 6,200,317 B1 | 3/2001 | Aalsma et al. |
| 6,234,956 B1 | 5/2001 | He et al. |
| 6,241,730 B1 | 6/2001 | Alby |
| 6,245,075 B1 | 6/2001 | Betz et al. |
| 6,245,076 B1 * | 6/2001 | Yan .................. A61F 2/95 606/108 |
| 6,315,784 B1 | 11/2001 | Djurovic |
| 6,319,255 B1 | 11/2001 | Grundei et al. |
| 6,331,744 B1 | 12/2001 | Chen et al. |
| 6,336,929 B1 | 1/2002 | Justin |
| 6,343,568 B1 | 2/2002 | McClasky |
| 6,358,283 B1 | 3/2002 | Hogfors et al. |
| 6,375,682 B1 | 4/2002 | Fleischmann et al. |
| 6,389,187 B1 | 5/2002 | Greenaway et al. |
| 6,400,980 B1 | 6/2002 | Lemelson |
| 6,402,753 B1 | 6/2002 | Cole et al. |
| 6,409,175 B1 | 6/2002 | Evans et al. |
| 6,416,516 B1 | 7/2002 | Stauch et al. |
| 6,499,907 B1 | 12/2002 | Baur |
| 6,500,110 B1 | 12/2002 | Davey et al. |
| 6,508,820 B2 | 1/2003 | Bales |
| 6,510,345 B1 | 1/2003 | Van Bentem |
| 6,537,196 B1 | 3/2003 | Creighton, IV et al. |
| 6,554,831 B1 | 4/2003 | Rivard et al. |
| 6,565,573 B1 | 5/2003 | Ferrante et al. |
| 6,565,576 B1 | 5/2003 | Stauch et al. |
| 6,582,313 B2 | 6/2003 | Perrow |
| 6,583,630 B2 | 6/2003 | Mendes et al. |
| 6,616,669 B2 | 9/2003 | Ogilvie et al. |
| 6,626,917 B1 | 9/2003 | Craig |
| 6,656,135 B2 | 12/2003 | Zogbi et al. |
| 6,656,194 B1 | 12/2003 | Gannoe et al. |
| 6,667,725 B1 | 12/2003 | Simons et al. |
| 6,673,079 B1 | 1/2004 | Kane |
| 6,702,816 B2 | 3/2004 | Buhler |
| 6,706,042 B2 | 3/2004 | Taylor |
| 6,709,293 B2 | 3/2004 | Mori et al. |
| 6,730,087 B1 | 5/2004 | Butsch |
| 6,761,503 B2 | 7/2004 | Breese |
| 6,769,499 B2 | 8/2004 | Cargill et al. |
| 6,789,442 B2 | 9/2004 | Forch |
| 6,796,984 B2 | 9/2004 | Soubeiran |
| 6,802,844 B2 | 10/2004 | Ferree |
| 6,809,434 B1 | 10/2004 | Duncan et al. |
| 6,835,207 B2 | 12/2004 | Zacouto et al. |
| 6,852,113 B2 | 2/2005 | Nathanson et al. |
| 6,918,838 B2 | 7/2005 | Schwarzler et al. |
| 6,918,910 B2 | 7/2005 | Smith et al. |
| 6,921,400 B2 | 7/2005 | Sohngen |
| 6,923,951 B2 | 8/2005 | Contag et al. |
| 6,971,143 B2 | 12/2005 | Domroese |
| 7,001,346 B2 | 2/2006 | White |
| 7,008,425 B2 | 3/2006 | Phillips |

(56) References Cited

U.S. PATENT DOCUMENTS

| | | |
|---|---|---|
| 7,011,658 B2 | 3/2006 | Young |
| 7,029,472 B1 | 4/2006 | Fortin |
| 7,029,475 B2 | 4/2006 | Panjabi |
| 7,041,105 B2 | 5/2006 | Michelson |
| 7,060,080 B2 | 6/2006 | Bachmann |
| 7,063,706 B2 | 6/2006 | Wittenstein |
| 7,105,029 B2 | 9/2006 | Doubler et al. |
| 7,105,968 B2 | 9/2006 | Nissen |
| 7,114,501 B2 | 10/2006 | Johnson et al. |
| 7,115,129 B2 | 10/2006 | Heggeness |
| 7,135,022 B2 | 11/2006 | Kosashvili et al. |
| 7,160,312 B2 | 1/2007 | Saadat |
| 7,163,538 B2 | 1/2007 | Altarac et al. |
| 7,189,005 B2 | 3/2007 | Ward |
| 7,191,007 B2 | 3/2007 | Desai et al. |
| 7,218,232 B2 | 5/2007 | DiSilvestro et al. |
| 7,238,191 B2 | 7/2007 | Bachmann |
| 7,241,300 B2 | 7/2007 | Sharkawy et al. |
| 7,243,719 B2 | 7/2007 | Baron et al. |
| 7,255,682 B1 | 8/2007 | Bartol, Jr. et al. |
| 7,282,023 B2 | 10/2007 | Frering |
| 7,285,087 B2 | 10/2007 | Moaddeb et al. |
| 7,302,015 B2 | 11/2007 | Kim et al. |
| 7,302,858 B2 | 12/2007 | Walsh et al. |
| 7,314,443 B2 | 1/2008 | Jordan et al. |
| 7,333,013 B2 | 2/2008 | Berger |
| 7,357,037 B2 | 4/2008 | Hnat et al. |
| 7,357,635 B2 | 4/2008 | Belfor et al. |
| 7,360,542 B2 | 4/2008 | Nelson et al. |
| 7,390,007 B2 | 6/2008 | Helms et al. |
| 7,390,294 B2 | 6/2008 | Hassler, Jr. |
| 7,402,134 B2 | 7/2008 | Moaddeb et al. |
| 7,402,176 B2 | 7/2008 | Malek |
| 7,429,259 B2 | 9/2008 | Cadeddu et al. |
| 7,445,010 B2 | 11/2008 | Kugler et al. |
| 7,458,981 B2 | 12/2008 | Fielding et al. |
| 7,485,149 B1 | 2/2009 | White |
| 7,489,495 B2 | 2/2009 | Stevenson |
| 7,530,981 B2 | 5/2009 | Kutsenko |
| 7,531,002 B2 | 5/2009 | Sutton et al. |
| 7,553,298 B2 | 6/2009 | Hunt et al. |
| 7,559,951 B2 | 7/2009 | DiSilvestro et al. |
| 7,561,916 B2 | 7/2009 | Hunt et al. |
| 7,611,526 B2 | 11/2009 | Carl et al. |
| 7,618,435 B2 | 11/2009 | Opolski |
| 7,658,754 B2 | 2/2010 | Zhang et al. |
| 7,666,184 B2 | 2/2010 | Stauch |
| 7,666,210 B2 | 2/2010 | Franck et al. |
| 7,678,136 B2 | 3/2010 | Doubler et al. |
| 7,678,139 B2 | 3/2010 | Garamszegi et al. |
| 7,708,737 B2 | 5/2010 | Kraft et al. |
| 7,708,762 B2 | 5/2010 | McCarthy et al. |
| 7,727,143 B2 | 6/2010 | Birk et al. |
| 7,753,913 B2 | 7/2010 | Szakelyhidi, Jr. et al. |
| 7,753,915 B1 | 7/2010 | Eksler et al. |
| 7,762,998 B2 | 7/2010 | Birk et al. |
| 7,763,080 B2 | 7/2010 | Southworth |
| 7,766,855 B2 | 8/2010 | Miethke |
| 7,775,215 B2 | 8/2010 | Hassler, Jr. et al. |
| 7,776,068 B2 | 8/2010 | Ainsworth et al. |
| 7,776,075 B2 | 8/2010 | Bruneau et al. |
| 7,787,958 B2 | 8/2010 | Stevenson |
| 7,794,476 B2 | 9/2010 | Wisnewski |
| 7,811,328 B2 | 10/2010 | Molz, IV et al. |
| 7,835,779 B2 | 11/2010 | Anderson et al. |
| 7,837,691 B2 | 11/2010 | Cordes et al. |
| 7,862,586 B2 | 1/2011 | Malek |
| 7,867,235 B2 | 1/2011 | Fell et al. |
| 7,875,033 B2 | 1/2011 | Richter et al. |
| 7,901,381 B2 | 3/2011 | Birk et al. |
| 7,909,852 B2 | 3/2011 | Boomer et al. |
| 7,918,844 B2 | 4/2011 | Byrum et al. |
| 7,938,841 B2 | 5/2011 | Sharkawy et al. |
| 7,985,256 B2 | 7/2011 | Grotz et al. |
| 7,988,709 B2 | 8/2011 | Clark et al. |
| 8,002,809 B2 | 8/2011 | Baynham |
| 8,011,308 B2 | 9/2011 | Picchio |
| 8,034,080 B2 | 10/2011 | Malandain et al. |
| 8,043,299 B2 | 10/2011 | Conway |
| 8,043,338 B2 | 10/2011 | Dant |
| 8,057,473 B2 | 11/2011 | Orsak et al. |
| 8,057,513 B2 | 11/2011 | Kohm et al. |
| 8,083,741 B2 | 12/2011 | Morgan et al. |
| 8,092,499 B1 | 1/2012 | Roth |
| 8,095,317 B2 | 1/2012 | Ekseth et al. |
| 8,105,360 B1 | 1/2012 | Connor |
| 8,114,158 B2 | 2/2012 | Carl et al. |
| 8,123,805 B2 | 2/2012 | Makower et al. |
| 8,133,280 B2 | 3/2012 | Voellmicke et al. |
| 8,147,549 B2 | 4/2012 | Metcalf, Jr. et al. |
| 8,162,897 B2 | 4/2012 | Byrum |
| 8,162,979 B2 | 4/2012 | Sachs et al. |
| 8,177,789 B2 | 5/2012 | Magill et al. |
| 8,197,490 B2 | 6/2012 | Pool et al. |
| 8,211,149 B2 | 7/2012 | Justis |
| 8,211,151 B2 | 7/2012 | Schwab et al. |
| 8,221,420 B2 | 7/2012 | Keller |
| 8,226,690 B2 | 7/2012 | Altarac et al. |
| 8,236,002 B2 | 8/2012 | Fortin et al. |
| 8,241,331 B2 | 8/2012 | Arnin |
| 8,246,630 B2 | 8/2012 | Manzi et al. |
| 8,252,063 B2 | 8/2012 | Stauch |
| 8,267,969 B2 | 9/2012 | Altarac et al. |
| 8,278,941 B2 | 10/2012 | Kroh et al. |
| 8,282,671 B2 | 10/2012 | Connor |
| 8,323,290 B2 | 12/2012 | Metzger et al. |
| 8,357,182 B2 | 1/2013 | Seme |
| 8,366,628 B2 | 2/2013 | Denker et al. |
| 8,372,078 B2 | 2/2013 | Collazo |
| 8,382,756 B2 | 2/2013 | Pool et al. |
| 8,386,018 B2 | 2/2013 | Stauch et al. |
| 8,394,124 B2 | 3/2013 | Biyani |
| 8,403,958 B2 | 3/2013 | Schwab |
| 8,414,584 B2 | 4/2013 | Brigido |
| 8,425,608 B2 | 4/2013 | Dewey et al. |
| 8,435,268 B2 | 5/2013 | Thompson et al. |
| 8,439,926 B2 | 5/2013 | Bojarski et al. |
| 8,444,693 B2 | 5/2013 | Reiley |
| 8,469,908 B2 | 6/2013 | Asfora |
| 8,470,004 B2 | 6/2013 | Reiley |
| 8,486,070 B2 | 7/2013 | Morgan et al. |
| 8,486,076 B2 | 7/2013 | Chavarria et al. |
| 8,486,147 B2 | 7/2013 | De Villiers et al. |
| 8,494,805 B2 | 7/2013 | Roche et al. |
| 8,496,662 B2 | 7/2013 | Novak et al. |
| 8,518,062 B2 | 8/2013 | Cole et al. |
| 8,523,866 B2 | 9/2013 | Sidebotham et al. |
| 8,529,474 B2 | 9/2013 | Gupta et al. |
| 8,529,606 B2 | 9/2013 | Alamin et al. |
| 8,529,607 B2 | 9/2013 | Alamin et al. |
| 8,556,901 B2 | 10/2013 | Anthony et al. |
| 8,556,911 B2 | 10/2013 | Mehta et al. |
| 8,556,975 B2 | 10/2013 | Ciupik et al. |
| 8,562,653 B2 | 10/2013 | Alamin et al. |
| 8,568,457 B2 | 10/2013 | Hunziker |
| 8,617,220 B2 | 10/2013 | Skaggs |
| 8,579,979 B2 | 11/2013 | Edie et al. |
| 8,585,595 B2 | 11/2013 | Heilman |
| 8,585,740 B1 | 11/2013 | Ross et al. |
| 8,591,549 B2 | 11/2013 | Lange |
| 8,591,553 B2 | 11/2013 | Eisermann et al. |
| 8,613,758 B2 | 12/2013 | Linares |
| 8,623,036 B2 | 1/2014 | Harrison et al. |
| 8,632,544 B2 | 1/2014 | Haaja et al. |
| 8,632,548 B2 | 1/2014 | Soubeiran |
| 8,632,563 B2 | 1/2014 | Nagase et al. |
| 8,636,771 B2 | 1/2014 | Butler et al. |
| 8,636,802 B2 | 1/2014 | Serhan et al. |
| 8,641,719 B2 | 2/2014 | Gephart et al. |
| 8,641,723 B2 | 2/2014 | Connor |
| 8,657,856 B2 | 2/2014 | Gephart et al. |
| 8,663,285 B2 | 3/2014 | Dall et al. |
| 8,663,287 B2 | 3/2014 | Butler et al. |
| 8,668,719 B2 | 3/2014 | Alamin et al. |

(56) References Cited

U.S. PATENT DOCUMENTS

| | | | |
|---|---|---|---|
| 8,709,090 B2 | 4/2014 | Makower et al. | |
| 8,734,488 B2 * | 5/2014 | Pool | A61B 17/707 |
| | | | 606/259 |
| 8,758,347 B2 | 6/2014 | Weiner et al. | |
| 8,758,355 B2 | 6/2014 | Fisher et al. | |
| 8,771,272 B2 | 7/2014 | LeCronier et al. | |
| 8,777,947 B2 | 7/2014 | Zahrly et al. | |
| 8,777,995 B2 | 7/2014 | McClintock et al. | |
| 8,790,343 B2 | 7/2014 | McClellan et al. | |
| 8,790,409 B2 | 7/2014 | Van den Heuvel et al. | |
| 8,828,058 B2 | 9/2014 | Elsebaie et al. | |
| 8,828,087 B2 | 9/2014 | Stone et al. | |
| 8,840,651 B2 | 9/2014 | Reiley | |
| 8,870,881 B2 | 10/2014 | Rezach et al. | |
| 8,870,959 B2 | 10/2014 | Arnin | |
| 8,915,915 B2 | 12/2014 | Harrison et al. | |
| 8,915,917 B2 | 12/2014 | Doherty et al. | |
| 8,920,422 B2 | 12/2014 | Homeier et al. | |
| 8,945,188 B2 | 2/2015 | Rezach et al. | |
| 8,961,521 B2 | 2/2015 | Keefer et al. | |
| 8,961,567 B2 | 2/2015 | Hunziker | |
| 8,968,402 B2 | 3/2015 | Myers et al. | |
| 8,992,527 B2 | 3/2015 | Guichet | |
| 9,022,917 B2 | 5/2015 | Kasic et al. | |
| 9,044,218 B2 | 6/2015 | Young | |
| 9,044,281 B2 | 6/2015 | Pool et al. | |
| 9,060,810 B2 | 6/2015 | Kercher et al. | |
| 9,078,703 B2 | 7/2015 | Arnin | |
| 9,078,711 B2 | 7/2015 | Quick | |
| 9,248,043 B2 | 2/2016 | Payne et al. | |
| 9,282,997 B2 | 3/2016 | Hunziker | |
| 9,445,720 B2 | 9/2016 | Janna et al. | |
| 9,730,612 B2 * | 8/2017 | Quick | H01F 27/2823 |
| 9,883,896 B2 | 2/2018 | Kim et al. | |
| 9,931,138 B2 | 4/2018 | Lynch et al. | |
| 10,314,619 B2 | 6/2019 | Roschak et al. | |
| 10,702,375 B2 | 7/2020 | Roholt et al. | |
| 10,835,290 B2 | 11/2020 | Cheng et al. | |
| 11,246,694 B2 | 2/2022 | Cheng | |
| 11,357,547 B2 | 6/2022 | Roschak et al. | |
| 2002/0050112 A1 | 5/2002 | Koch et al. | |
| 2002/0072758 A1 | 6/2002 | Reo et al. | |
| 2002/0164905 A1 | 11/2002 | Bryant | |
| 2003/0040671 A1 | 2/2003 | Somogyi et al. | |
| 2003/0144669 A1 | 7/2003 | Robinson | |
| 2003/0220643 A1 | 11/2003 | Ferree | |
| 2003/0220644 A1 | 11/2003 | Thelen et al. | |
| 2004/0011137 A1 | 1/2004 | Hnat et al. | |
| 2004/0011365 A1 | 1/2004 | Govari et al. | |
| 2004/0019353 A1 | 1/2004 | Freid et al. | |
| 2004/0023623 A1 | 2/2004 | Stauch et al. | |
| 2004/0055610 A1 | 3/2004 | Forsell | |
| 2004/0133219 A1 | 7/2004 | Forsell | |
| 2004/0138725 A1 | 7/2004 | Forsell | |
| 2004/0193266 A1 | 9/2004 | Meyer | |
| 2005/0034705 A1 | 2/2005 | McClendon | |
| 2005/0049617 A1 | 3/2005 | Chatlynne et al. | |
| 2005/0065529 A1 | 3/2005 | Liu et al. | |
| 2005/0090823 A1 | 4/2005 | Bartimus | |
| 2005/0159754 A1 | 7/2005 | Odrich | |
| 2005/0234448 A1 | 10/2005 | McCarthy | |
| 2005/0234462 A1 | 10/2005 | Hershberger | |
| 2005/0246034 A1 | 11/2005 | Soubeiran | |
| 2005/0261779 A1 | 11/2005 | Meyer | |
| 2005/0272976 A1 | 12/2005 | Tanaka et al. | |
| 2006/0004459 A1 | 1/2006 | Hazebrouck et al. | |
| 2006/0009767 A1 | 1/2006 | Kiester | |
| 2006/0036259 A1 | 2/2006 | Carl et al. | |
| 2006/0036323 A1 | 2/2006 | Carl et al. | |
| 2006/0036324 A1 | 2/2006 | Sachs et al. | |
| 2006/0047282 A1 | 3/2006 | Gordon | |
| 2006/0058792 A1 | 3/2006 | Hynes | |
| 2006/0069447 A1 | 3/2006 | DiSilvestro et al. | |
| 2006/0074448 A1 | 4/2006 | Harrison et al. | |
| 2006/0079897 A1 | 4/2006 | Harrison et al. | |
| 2006/0136062 A1 | 6/2006 | DiNello et al. |
| 2006/0142767 A1 | 6/2006 | Green et al. |
| 2006/0155279 A1 | 7/2006 | Ogilvie |
| 2006/0195087 A1 | 8/2006 | Sacher et al. |
| 2006/0195088 A1 | 8/2006 | Sacher et al. |
| 2006/0200134 A1 | 9/2006 | Freid et al. |
| 2006/0204156 A1 | 9/2006 | Takehara et al. |
| 2006/0235299 A1 | 10/2006 | Martinelli |
| 2006/0235424 A1 | 10/2006 | Vitale et al. |
| 2006/0241746 A1 | 10/2006 | Shaoulian et al. |
| 2006/0241767 A1 | 10/2006 | Doty |
| 2006/0249914 A1 | 11/2006 | Dulin |
| 2006/0271107 A1 | 11/2006 | Harrison et al. |
| 2006/0282073 A1 | 12/2006 | Simanovsky |
| 2006/0293683 A1 | 12/2006 | Stauch |
| 2007/0010814 A1 | 1/2007 | Stauch |
| 2007/0010887 A1 | 1/2007 | Williams et al. |
| 2007/0021644 A1 | 1/2007 | Woolson et al. |
| 2007/0031131 A1 | 2/2007 | Griffitts |
| 2007/0043376 A1 | 2/2007 | Leatherbury et al. |
| 2007/0050030 A1 | 3/2007 | Kim |
| 2007/0118215 A1 | 5/2007 | Moaddeb |
| 2007/0161984 A1 | 7/2007 | Cresina et al. |
| 2007/0173837 A1 | 7/2007 | Chan et al. |
| 2007/0179493 A1 | 8/2007 | Kim |
| 2007/0185374 A1 | 8/2007 | Kick et al. |
| 2007/0233098 A1 | 10/2007 | Mastrorio et al. |
| 2007/0239159 A1 | 10/2007 | Altarac et al. |
| 2007/0239161 A1 | 10/2007 | Giger et al. |
| 2007/0255088 A1 | 11/2007 | Jacobson et al. |
| 2007/0270803 A1 | 11/2007 | Giger et al. |
| 2007/0276368 A1 | 11/2007 | Trieu et al. |
| 2007/0276369 A1 | 11/2007 | Allard et al. |
| 2007/0276373 A1 | 11/2007 | Malandain |
| 2007/0276378 A1 | 11/2007 | Harrison et al. |
| 2007/0276493 A1 | 11/2007 | Malandain et al. |
| 2007/0288024 A1 | 12/2007 | Gollogly |
| 2007/0288183 A1 | 12/2007 | Bulkes et al. |
| 2008/0009792 A1 | 1/2008 | Henniges et al. |
| 2008/0015577 A1 | 1/2008 | Loeb |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0027436 A1 | 1/2008 | Cournoyer et al. |
| 2008/0033431 A1 | 2/2008 | Jung et al. |
| 2008/0033436 A1 | 2/2008 | Song et al. |
| 2008/0051784 A1 | 2/2008 | Gollogly |
| 2008/0082118 A1 | 4/2008 | Edidin et al. |
| 2008/0086128 A1 | 4/2008 | Lewis |
| 2008/0097487 A1 | 4/2008 | Pool et al. |
| 2008/0097496 A1 | 4/2008 | Chang et al. |
| 2008/0108995 A1 | 5/2008 | Conway et al. |
| 2008/0161933 A1 | 7/2008 | Grotz et al. |
| 2008/0167685 A1 | 7/2008 | Allard et al. |
| 2008/0172063 A1 | 7/2008 | Taylor |
| 2008/0177319 A1 | 7/2008 | Schwab |
| 2008/0177326 A1 | 7/2008 | Thompson |
| 2008/0190237 A1 | 8/2008 | Radinger et al. |
| 2008/0228186 A1 | 9/2008 | Gall et al. |
| 2008/0255615 A1 | 10/2008 | Vittur et al. |
| 2008/0272928 A1 | 11/2008 | Shuster |
| 2008/0275557 A1 | 11/2008 | Makower et al. |
| 2009/0030462 A1 | 1/2009 | Buttermann |
| 2009/0076597 A1 | 3/2009 | Dahlgren et al. |
| 2009/0082815 A1 | 3/2009 | Zylber et al. |
| 2009/0088803 A1 | 4/2009 | Justis et al. |
| 2009/0093820 A1 | 4/2009 | Trieu et al. |
| 2009/0093890 A1 | 4/2009 | Gelbart |
| 2009/0112263 A1 | 4/2009 | Pool et al. |
| 2009/0163780 A1 | 6/2009 | Tieu |
| 2009/0171356 A1 | 7/2009 | Klett |
| 2009/0192514 A1 | 7/2009 | Feinberg et al. |
| 2009/0198144 A1 | 8/2009 | Phillips et al. |
| 2009/0216113 A1 | 8/2009 | Meier et al. |
| 2009/0275984 A1 | 11/2009 | Kim et al. |
| 2010/0004654 A1 | 1/2010 | Schmitz et al. |
| 2010/0057127 A1 | 3/2010 | McGuire et al. |
| 2010/0094302 A1 | 4/2010 | Pool et al. |
| 2010/0094306 A1 | 4/2010 | Chang et al. |

(56) References Cited

U.S. PATENT DOCUMENTS

| | | |
|---|---|---|
| 2010/0100185 A1 | 4/2010 | Trieu et al. |
| 2010/0106192 A1 | 4/2010 | Barry |
| 2010/0114322 A1 | 5/2010 | Clifford et al. |
| 2010/0130941 A1 | 5/2010 | Conlon et al. |
| 2010/0137872 A1 | 6/2010 | Kam et al. |
| 2010/0145449 A1 | 6/2010 | Makower et al. |
| 2010/0145462 A1 | 6/2010 | Ainsworth et al. |
| 2010/0168751 A1 | 7/2010 | Anderson et al. |
| 2010/0249782 A1 | 9/2010 | Durham |
| 2010/0256626 A1 | 10/2010 | Muller et al. |
| 2010/0262239 A1 | 10/2010 | Boyden et al. |
| 2010/0318129 A1 | 12/2010 | Seme et al. |
| 2010/0331883 A1 | 12/2010 | Schmitz et al. |
| 2011/0004076 A1 | 1/2011 | Janna et al. |
| 2011/0057756 A1 | 3/2011 | Marinescu et al. |
| 2011/0060336 A1 | 3/2011 | Pool et al. |
| 2011/0066188 A1 | 3/2011 | Seme et al. |
| 2011/0098748 A1 | 4/2011 | Jangra |
| 2011/0152725 A1 | 6/2011 | Demir et al. |
| 2011/0196435 A1 | 8/2011 | Forsell |
| 2011/0202138 A1 | 8/2011 | Shenoy et al. |
| 2011/0238126 A1 | 9/2011 | Soubeiran |
| 2011/0257655 A1 | 10/2011 | Copf, Jr. |
| 2011/0284014 A1 | 11/2011 | Cadeddu et al. |
| 2011/0319755 A1 | 12/2011 | Stein et al. |
| 2012/0004494 A1 | 1/2012 | Payne et al. |
| 2012/0019341 A1 | 1/2012 | Gabay et al. |
| 2012/0019342 A1 | 1/2012 | Gabay et al. |
| 2012/0053633 A1 | 3/2012 | Stauch |
| 2012/0088953 A1 | 4/2012 | King |
| 2012/0109207 A1 | 5/2012 | Trieu |
| 2012/0116535 A1 | 5/2012 | Ratron et al. |
| 2012/0158061 A1 | 6/2012 | Koch et al. |
| 2012/0172883 A1 | 7/2012 | Sayago |
| 2012/0179215 A1 | 7/2012 | Soubeiran |
| 2012/0221106 A1 | 8/2012 | Makower et al. |
| 2012/0271353 A1 | 10/2012 | Barry |
| 2012/0296234 A1 | 11/2012 | Wilhelm et al. |
| 2012/0329882 A1 | 12/2012 | Messersmith et al. |
| 2013/0013066 A1 | 1/2013 | Landry et al. |
| 2013/0072932 A1 | 3/2013 | Stauch |
| 2013/0123847 A1 | 5/2013 | Anderson et al. |
| 2013/0138017 A1 | 5/2013 | Jundt et al. |
| 2013/0138154 A1 | 5/2013 | Reiley |
| 2013/0150863 A1 | 6/2013 | Baumgartner |
| 2013/0150889 A1 | 6/2013 | Fening et al. |
| 2013/0178903 A1 | 7/2013 | Abdou |
| 2013/0211521 A1 | 8/2013 | Shenoy et al. |
| 2013/0245692 A1 | 9/2013 | Hayes et al. |
| 2013/0253344 A1 | 9/2013 | Griswold et al. |
| 2013/0253587 A1 | 9/2013 | Carls et al. |
| 2013/0261672 A1 | 10/2013 | Horvath |
| 2013/0296863 A1 | 11/2013 | Globerman et al. |
| 2013/0296864 A1 | 11/2013 | Burley et al. |
| 2013/0296940 A1 | 11/2013 | Northcutt et al. |
| 2013/0325006 A1 | 12/2013 | Michelinie et al. |
| 2013/0325071 A1 | 12/2013 | Niemiec et al. |
| 2013/0338714 A1* | 12/2013 | Chang ............... A61B 17/7016 606/258 |
| 2014/0005788 A1 | 1/2014 | Haaja et al. |
| 2014/0025172 A1 | 1/2014 | Lucas et al. |
| 2014/0031870 A1 | 1/2014 | Chang et al. |
| 2014/0052134 A1 | 2/2014 | Orisek |
| 2014/0058392 A1 | 2/2014 | Mueckter et al. |
| 2014/0058450 A1 | 2/2014 | Arlet |
| 2014/0066987 A1 | 3/2014 | Hestad et al. |
| 2014/0088715 A1 | 3/2014 | Ciupik |
| 2014/0128920 A1 | 5/2014 | Kantelhardt |
| 2014/0163664 A1 | 6/2014 | Goldsmith |
| 2014/0236234 A1 | 8/2014 | Kroll et al. |
| 2014/0236311 A1 | 8/2014 | Vicatos et al. |
| 2014/0250674 A1* | 9/2014 | Pool ..................... A61B 90/06 29/525.11 |
| 2014/0257412 A1 | 9/2014 | Patty et al. |
| 2014/0277446 A1 | 9/2014 | Clifford et al. |
| 2014/0296918 A1 | 10/2014 | Fening et al. |
| 2014/0303538 A1 | 10/2014 | Baym et al. |
| 2014/0303539 A1 | 10/2014 | Baym et al. |
| 2014/0358150 A1 | 12/2014 | Kaufman et al. |
| 2015/0025587 A1 | 1/2015 | Kim et al. |
| 2015/0105782 A1 | 4/2015 | D'Lima et al. |
| 2015/0105824 A1 | 4/2015 | Moskowitz et al. |
| 2015/0250505 A1 | 9/2015 | Ross |
| 2016/0058483 A1 | 3/2016 | Stauch |
| 2016/0113683 A1 | 4/2016 | Cheng |
| 2017/0035470 A1* | 2/2017 | Pool ..................... A61B 17/846 |
| 2017/0049489 A1 | 2/2017 | Pool |
| 2017/0172624 A1 | 6/2017 | Brunner et al. |
| 2017/0333080 A1 | 11/2017 | Roschak |
| 2018/0221062 A1* | 8/2018 | Hunziker ........... A61B 1/00158 |
| 2018/0296256 A1* | 10/2018 | Beckett .............. A61B 17/7233 |
| 2019/0015138 A1* | 1/2019 | Schwardt ............. A61B 17/66 |
| 2019/0254712 A1 | 8/2019 | Roschak et al. |
| 2020/0187989 A1 | 6/2020 | Hunziker |

FOREIGN PATENT DOCUMENTS

| | | |
|---|---|---|
| DE | 1541262 A1 | 6/1969 |
| DE | 8515687 U1 | 12/1985 |
| DE | 19626230 A1 | 1/1998 |
| DE | 19745654 A1 | 4/1999 |
| DE | 102005045070 A1 | 4/2007 |
| EP | 0663184 A1 | 7/1995 |
| EP | 1905388 A1 | 4/2008 |
| FR | 2901991 A1 | 12/2007 |
| FR | 2900563 B1 | 8/2008 |
| FR | 2892617 B1 | 9/2008 |
| FR | 2916622 B1 | 9/2009 |
| FR | 2961386 B1 | 12/2011 |
| JP | H0956736 | 3/1997 |
| JP | 2002500063 A | 1/2002 |
| WO | WO1998044858 A1 | 10/1998 |
| WO | WO1999051160 A1 | 10/1999 |
| WO | WO2001024697 A1 | 4/2001 |
| WO | WO2001045485 A3 | 6/2001 |
| WO | WO2001045487 A2 | 6/2001 |
| WO | WO2001067973 A2 | 9/2001 |
| WO | WO2001078614 A1 | 10/2001 |
| WO | WO2007013059 A3 | 2/2007 |
| WO | WO2007015239 A3 | 2/2007 |
| WO | WO2011116158 A3 | 9/2011 |
| WO | WO2013119528 A1 | 8/2013 |
| WO | WO2014040013 A1 | 3/2014 |
| WO | 2020055874 A1 | 3/2020 |
| WO | 2020069627 A1 | 4/2020 |
| WO | 2020/163800 A1 | 8/2020 |
| WO | 2022/015898 A1 | 1/2022 |

OTHER PUBLICATIONS

Abe et al., "Experimental external fixation combined with percutaneous discectomy in the management of scoliosis.", Spine, 1999, pp. 646-653, 24, No. 7.

Ahlbom et al., "Guidelines for limiting exposure to time-varying electric, magnetic, and electromagnetic fields (up to 300 GHZ). International Commission on Non-Ionizing Radiation Protection.", Health Physics, 1998, pp. 494-522, 74, No. 4.

Amer et al., "Evaluation of treatment of late-onset tibia vara using gradual angulation translation high tibial osteotomy", ACTA Orthopaedica Belgica, 2010, pp. 360-366, 76, No. 3.

Angrisani et al., "Lap-Band® Rapid Port™M System: Preliminary results in 21 patients", Obesity Surgery, 2005, p. 936, 15, No. 7.

Baumgart et al., "A fully implantable, programmable distraction nail (Fitbone)—new perspectives for corrective and reconstructive limb surgery.", Practice of Intramedullary Locked Nails, 2006, pp. 189-198.

Baumgart et al., "The bioexpandable prosthesis: A new perspective after resection of malignant bone tumors in children.", J Pediatr Hematol Oncol, 2005, pp. 452-455, 27, No. 8.

Bodó et al., "Development of a tension-adjustable implant for anterior cruciate ligament reconstruction.", Eklem Hastaliklari ve

(56) References Cited

OTHER PUBLICATIONS

Cerrahisi—Joint Diseases and Related Surgery, 2008, pp. 27-32, 19, No. 1.

Boudjemline et al., "Off-label use of an adjustable gastric banding system for pulmonary artery banding.", The Journal of Thoracic and Cardiovascular Surgery, 2006, pp. 1130-1135, 131, No. 5.

Brown et al., "Single port surgery and the Dundee Endocone.", SAGES Annual Scientific Sessions: Emerging Technology Poster Abstracts, 2007, ETP007, pp. 323-324.

Buchowski et al., "Temporary internal distraction as an aid to correction of severe scoliosis", J Bone Joint Surg Am, 2006, pp. 2035-2041, 88-A, No. 9.

Burghardt et al., "Mechanical failure of the Intramedullary Skeletal Kinetic Distractor in limb lengthening.", J Bone Joint Surg Br, 2011, pp. 639-643, 93-B, No. 5.

Burke, "Design of a minimally invasive non fusion device for the surgical management of scoliosis in the skeletally immature", Studies in Health Technology and Informatics, 2006, pp. 378-384, 123.

Carter et al., "A cumulative damage model for bone fracture.", Journal of Orthopaedic Research, 1985, pp. 84-90, 3, No. 1.

Chapman et al., "Laparoscopic adjustable gastric banding in the treatment of obesity: A systematic literature review.", Surgery, 2004, pp. 326-351, 135, No. 3.

Cole et al., "Operative technique intramedullary skeletal kinetic distractor: Tibial surgical technique.", Orthofix, 2005.

Cole et al., "The intramedullary skeletal kinetic distractor (ISKD): first clinical results of a new intramedullary nail for lengthening of the femur and tibia.", Injury, 2001, pp. S-D-129-S-D-139, 32.

Dailey et al., "A novel intramedullary nail for micromotion stimulation of tibial fractures.", Clinical Biomechanics, 2012, pp. 182-188, 27, No. 2.

Daniels et al., "A new method for continuous intraoperative measurement of Harrington rod loading patterns.", Annals of Biomedical Engineering, 1984, pp. 233-246, 12, No. 3.

De Giorgi et al., "Cotrel-Dubousset instrumentation for the treatment of severe scoliosis.", European Spine Journal, 1999, pp. 8-15, No. 1.

Dorsey et al., "The stability of three commercially available implants used in medial opening wedge high tibial osteotomy.", Journal of Knee Surgery, 2006, pp. 95-98, 19, No. 2.

Edeland et al., "Instrumentation for distraction by limited surgery in scoliosis treatment.", Journal of Biomedical Engineering, 1981, pp. 143-146, 3, No. 2.

Elsebaie, "Single growing rods (Review of 21 cases). Changing the foundations: Does it affect the results?", Journal of Child Orthop, 2007, 1:258.

Ember et al., "Distraction forces required during growth rod lengthening.", J of Bone Joint Surg BR, 2006, p. 229, 88-B, No. Suppl. II.

European Patent Office, "Observations by a third party under Article 115 EPC in EP08805612 by Soubeiran.", 2010.

Fabry et al., "A technique for prevention of port complications after laparoscopic adjustable silicone gastric banding.", Obesity Surgery, 2002, pp. 285-288, 12, No. 2.

Fried et al., "In vivo measurements of different gastric band pressures towards the gastric wall at the stoma region.", Obesity Surgery, 2004, p. 914, 14, No. 7.

Gao et al., CHD7 gene polymorphisms are associated with susceptibility to idiopathic scoliosis, American Journal of Human Genetics, 2007, pp. 957-965, 80.

Gebhart et al., "Early clinical experience with a custom made growing endoprosthesis in children with malignant bone tumors of the lower extremity actioned by an external permanent magnet; The Phenix M. system", International Society of Limb Salvage 14th International Symposium on Limb Salvage. Sep. 3, 2007, Hamburg, Germany. (2 pages).

Gillespie et al. "Harrington instrumentation without fusion.", J Bone Joint Surg Br, 1981, p. 461, 63-B, No. 3.

Goodship et al., "Strain rate and timing of stimulation in mechanical modulation of fracture healing.", Clinical Orthopaedics and Related Research, 1998, pp. S105-S115, No. 355S.

Grass et al., "Intermittent distracting rod for correction of high neurologic risk congenital scoliosis.", Spine, 1997, pp. 1922-1927, 22, No. 16.

Gray, "Gray's anatomy of the human body.", http://education.yahoo.com/reference/gray/subjects/subject/128, published Jul. 1, 2007.

Grimer et al. "Non-invasive extendable endoprostheses for children—Expensive but worth it!", International Society of Limb Salvage 14th International Symposium on Limb Salvage, 2007.

Grünert, "The development of a totally implantable electronic sphincter." (translated from the German "Die Entwicklung eines total implantierbaren elektronischen Sphincters"), Langenbecks Archiv fur Chirurgie, 1969, pp. 1170-1174, 325.

Guichet et al. "Gradual femoral lengthening with the Albizzia intramedullary nail", J Bone Joint Surg Am, 2003, pp. 838-848, 85-A, No. 5.

Gupta et al., "Non-invasive distal femoral expandable endoprosthesis for limb-salvage surgery in paediatric tumours.", J Bone Joint Surg Br, 2006, pp. 649-654, 88-B, No. 5.

Hankemeier et al., "Limb lengthening with the Intramedullary Skeletal Kinetic Distractor (ISKD).", Oper Orthop Traumatol, 2005, pp. 79-101, 17, No. 1.

Harrington, "Treatment of scoliosis. Correction and internal fixation by spine instrumentation.", J Bone Joint Surg Am, 1962, pp. 591-610, 44-A, No. 4.

Hennig et al., "The safety and efficacy of a new adjustable plate used for proximal tibial opening wedge osteotomy in the treatment of unicompartmental knee osteoarthrosis.", Journal of Knee Surgery, 2007, pp. 6-14, 20, No. 1.

Hofmeister et al., "Callus distraction with the Albizzia nail.", Practice of Intramedullary Locked Nails, 2006, pp. 211-215.

Horbach et al., "First experiences with the routine use of the Rapid Port™ system with the Lap-Band®.", Obesity Surgery, 2006, p. 418, 16, No. 4.

Hyodo et al., "Bone transport using intramedullary fixation and a single flexible traction cable.", Clinical Orthopaedics and Related Research, 1996, pp. 256-268, 325.

International Commission on Non-Ionizing Radiation Protection, "Guidelines on limits of exposure to static magnetic fields." Health Physics, 2009, pp. 504-514, 96, No. 4.

INVIS®/Lamello Catalog, 2006, Article No. 68906A001 GB.

Kasliwal et al., "Management of high-grade spondylolisthesis.", Neurosurgery Clinics of North America, 2013, pp. 275-291, 24, No. 2.

Kenawey et al., "Leg lengthening using intramedullay skeletal kinetic distractor: Results of 57 consecutive applications.", Injury, 2011, pp. 150-155, 42, No. 2.

Kent et al., "Assessment and correction of femoral malrotation following intramedullary nailing of the femur.", Acta Orthop Belg, 2010, pp. 580-584, 76, No. 5.

Klemme et al., "Spinal instrumentation without fusion for progressive scoliosis in young children", Journal of Pediatric Orthopaedics. 1997, pp. 734-742, 17, No. 6.

Korenkov et al., "Port function after laparoscopic adjustable gastric banding for morbid obesity.", Surgical Endoscopy, 2003, pp. 1068-1071, 17, No. 7.

Krieg et al., "Leg lengthening with a motorized nail in adolescents.", Clinical Orthopaedics and Related Research, 2008, pp. 189-197, 466, No. 1.

Kucukkaya et al., "The new intramedullary cable bone transport technique.", Journal of Orthopaedic Trauma, 2009, pp. 531-536, 23, No. 7.

Lechner et al., "In vivo band manometry: A new method in band adjustment", Obesity Surgery, 2005, p. 935, 15, No. 7.

Lechner et al., "Intra-band manometry for band adjustments: The basics", Obesity Surgery, 2006, pp. 417-418, 16, No. 4.

Li et al., "Bone transport over an intramedullary nail: A case report with histologic examination of the regenerated segment.", Injury, 1999, pp. 525-534, 30, No. 8.

(56) References Cited

OTHER PUBLICATIONS

Lonner, "Emerging minimally invasive technologies for the management of scoliosis.", Orthopedic Clinics of North America, 2007, pp. 431-440, 38, No. 3.
Matthews et al., "Magnetically adjustable intraocular lens.", Journal of Cataract and Refractive Surgery, 2003, pp. 2211-2216, 29, No. 11.
Micromotion, "Micro Drive Engineering. General catalogue.", 2009, pp. 14-24.
Mineiro et al., "Subcutaneous rodding for progressive spinal curvatures: Early results.", Journal of Pediatric Orthopaedics, 2002, pp. 290-295, 22, No. 3.
Moe et al., "Harrington instrumentation without fusion plus external orthotic support for the treatment of difficult curvature problems in young children.", Clinical Orthopaedics and Related Research, 1984, pp. 35-45, 185.
Montague et al., "Magnetic gear dynamics for servo control.", Melecon 2010—2010 15th IEEE Mediterranean Electrotechnical Conference, Valletta, 2010, pp. 1192-1197.
Montague et al., "Servo control of magnetic gears.", IEEE/ASME Transactions on Mechatronics, 2012, pp. 269-278, 17, No. 2.
Nachemson et al., "Intravital wireless telemetry of axial forces in Harrington distraction rods in patients with idiopathic scoliosis.", The Journal of Bone and Joint Surgery, 1971, pp. 445-465, 53, No. 3.
Nachlas et al., "The cure of experimental scoliosis by directed growth control.", The Journal of Bone and Joint Surgery, 1951, pp. 24-34, 33-A, No. 1.
Newton et al., "Fusionless scoliosis correction by anterolateral tethering ... can it work ?. ", 39th Annual Scoliosis Research Society Meeting, 2004.
Oh et al., "Bone transport over an intramedullary nail for reconstruction of long bone defects in tibia.", Archives of Orthopaedic and Trauma Surgery, 2008, pp. 801-808, 128, No. 8.
Ozcivici et al., "Mechanical signals as anabolic agents in bone.", Nature Reviews Rheumatology, 2010, pp. 50-59, 6, No. 1.
Piorkowski et al., Preventing Port Site Inversion in Laparoscopic Adjustable Gastric Banding, Surgery for Obesity and Related Diseases, 2007, 3(2), pp. 159-162, Elsevier; New York, U.S.A.
Prontes, "Longest bone in body.", eHow.com, 2012.
Rathjen et al., "Clinical and radiographic results after implant removal in idiopathic scoliosis.", Spine, 2007, pp. 2184-2188, 32, No. 20.
Ren et al., "Laparoscopic adjustable gastric banding: Surgical technique", Journal of Laparoendoscopic & Advanced Surgical Techniques, 2003, pp. 257-263, 13, No. 4.
Reyes-Sanchez et al., "External fixation for dynamic correction of severe scoliosis", The Spine Journal, 2005, pp. 418-426, 5, No. 4.
Rinsky et al., "Segmental instrumentation without fusion in children with progressive scoliosis.", Journal of Pediatric Orthopedics, 1985, pp. 687-690, 5, No. 6.
Rode et al., "A simple way to adjust bands under radiologic control", Obesity Surgery, 2006, p. 418, 16, No. 4.
Schmerling et al., "Using the shape recovery of nitinol in the Harrington rod treatment of scoliosis.", Journal of Biomedical Materials Research, 1976, pp. 879-892, 10, No. 6.
Scott et al., "Transgastric, transcolonic and transvaginal cholecystectomy using magnetically anchored instruments.", SAGES Annual Scientific Sessions, Poster Abstracts, Apr. 18-22, 2007, P511, p. 306.
Sharke, "The machinery of life", Mechanical Engineering Magazine, Feb. 2004, Printed from Internet site Oct. 24, 2007 http://www.memagazine.org/contents/current/features/moflife/moflife.html.
Shiha et al., "Ilizarov gradual correction of genu varum deformity in adults.", Acta Orthop Belg, 2009, pp. 784-791, 75, No. 6.
Simpson et al., "Femoral lengthening with the intramedullary skeletal kinetic distractor.", Journal of Bone and Joint Surgery, 2009, pp. 955-961, 91-B, No. 7.
Smith, "The use of growth-sparing instrumentation in pediatric spinal deformity.", Orthopedic Clinics of North America, 2007, pp. 547-552, 38, No. 4.
Soubeiran et al. "The Phenix M System, a fully implanted non-invasive lengthening device externally controllable through the skin with a palm size permanent magnet. Applications in limb salvage." International Society of Limb Salvage 14th International Symposium on Limb Salvage, Sep. 13, 2007, Hamburg, Germany. (2 pages).
Soubeiran et al., "The Phenix M System. A fully implanted lengthening device externally controllable through the skin with a palm size permanent magnet; Applications to pediatric orthopaedics", 6th European Research Conference in Pediatric Orthopaedics, Oct. 6, 2006, Toulouse, France (7 pages).
Stokes et al., "Reducing radiation exposure in early-onset scoliosis surgery patients: Novel use of ultrasonography to measure lengthening in magnetically-controlled growing rods. Prospective validation study and assessment of clinical algorithm", 20th International Meeting on Advanced Spine Techniques, Jul. 11, 2013. Vancouver, Canada. Scoliosis Research Society.
Sun et al., "Masticatory mechanics of a mandibular distraction osteogenesis site: Interfragmentary micromovement.", Bone, 2007, pp. 188-196, 41, No. 2.
Synthes Spine, "VEPTR II. Vertical Expandable Prosthetic Titanium Rib II: Technique Guide.", 2008, 40 pgs.
Synthes Spine, "VEPTR Vertical Expandable Prosthetic Titanium Rib, Patient Guide.", 2005, 26 pgs.
Takaso et al., "New remote-controlled growing-rod spinal instrumentation possibly applicable for scoliosis in young children.", Journal of Orthopaedic Science, 1998, pp. 336-340, 3, No. 6.
Teli et al., "Measurement of forces generated during distraction of growing rods.", Journal of Children's Orthopaedics, 2007, pp. 257-258, 1, No. 4.
Tello, "Harrington instrumentation without arthrodesis and consecutive distraction program for young children with severe spinal deformities: Experience and technical details.", The Orthopedic Clinics of North America, 1994, pp. 333-351, 25, No. 2.
Thaller et al., "Limb lengthening with fully implantable magnetically actuated mechanical nails (PHENIX®)—Preliminary results.", Injury, 2014 (E-published Oct. 28, 2013), pp. S60-S65, 45.
Thompson et al., "Early onset scoliosis: Future directions", 2007, J Bone Joint Surg Am, pp. 163-166, 89-A, Suppl 1.
Thompson et al., "Growing rod techniques in early-onset scoliosis", Journal of Pediatric Orthopedics, 2007, pp. 354-361, 27, No. 3.
Thonse et al., "Limb lengthening with a fully implantable, telescopic, intramedullary nail.", Operative Techniques in Orthopedics, 2005, pp. 355-362, 15, No. 4.
Trias et al., "Dynamic loads experienced in correction of idiopathic scoliosis using two types of Harrington rods.", Spine, 1979, pp. 228-235, 4, No. 3.
Verkerke et al., "An extendable modular endoprosthetic system for bone tumor management in the leg", Journal of Biomedical Engineering, 1990, pp. 91-96, 12, No. 2.
Verkerke et al., "Design of a lengthening element for a modular femur endoprosthetic system", Proceedings of the Institution of Mechanical Engineers Part H: Journal of Engineering in Medicine, 1989, pp. 97-102, 203, No. 2.
Verkerke et al., "Development and test of an extendable endoprosthesis for bone reconstruction in the leg.", The International Journal of Artificial Organs, 1994, pp. 155-162, 17, No. 3.
Weiner et al., "Initial clinical experience with telemetrically adjustable gastric banding", Surgical Technology International, 2005, pp. 63-69, 15.
Wenger, "Spine jack operation in the correction of scoliotic deformity: A direct intrathoracic attack to straighten the laterally bent spine: Preliminary report", Arch Surg, 1961, pp. 123-132 (901-910), 83, No. 6.
White, III et al., "The clinical biomechanics of scoliosis.", Clinical Orthopaedics and Related Research, 1976, pp. 100-112, 118.
Yonnet, "A new type of permanent magnet coupling.", IEEE Transactions on Magnetics, 1981, pp. 2991-2993, 17, No. 6.
Yonnet, "Passive magnetic bearings with permanent magnets.", IEEE Transactions on Magnetics, 1978, pp. 803-805, 14, No. 5.

(56) References Cited

OTHER PUBLICATIONS

Zheng et al., "Force and torque characteristics for magnetically driven blood pump.", Journal of Magnetism and Magnetic Materials, 2002, pp. 292-302, 241, No. 2.

* cited by examiner

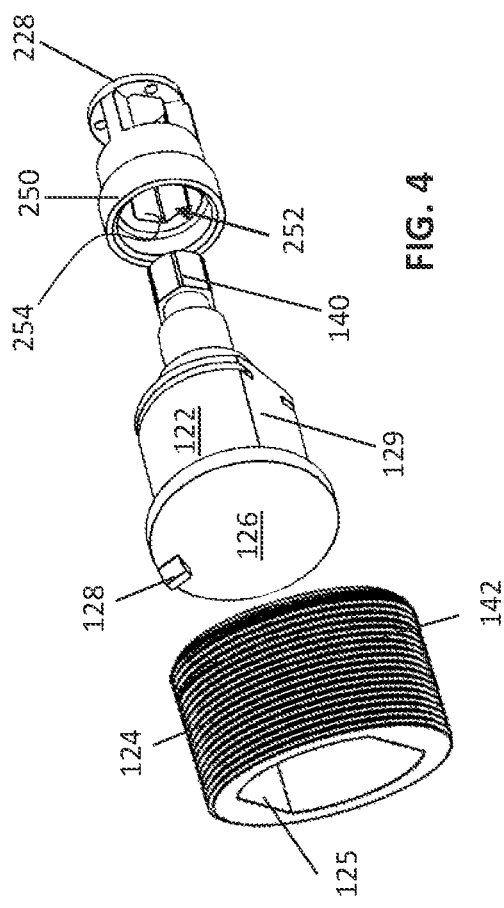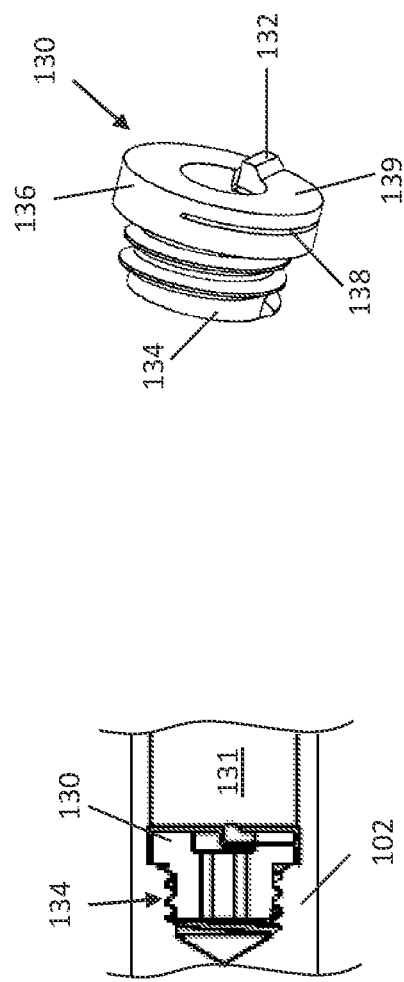

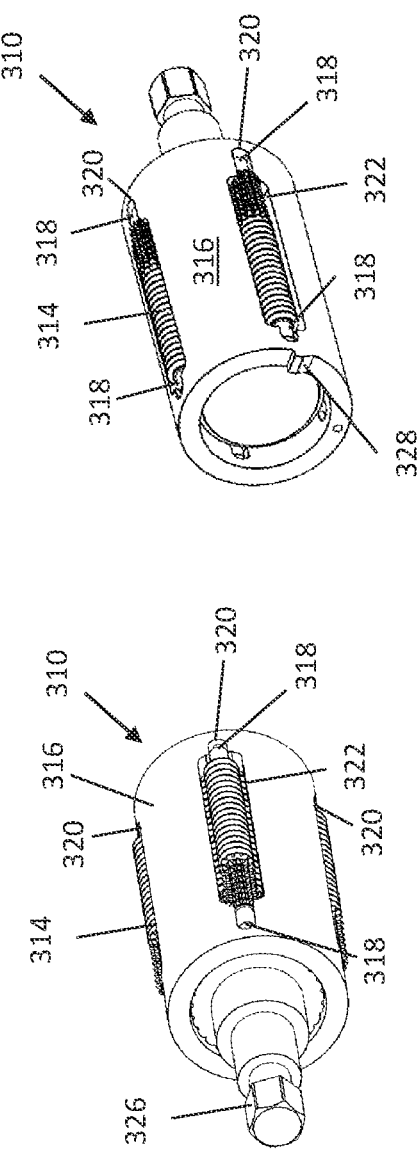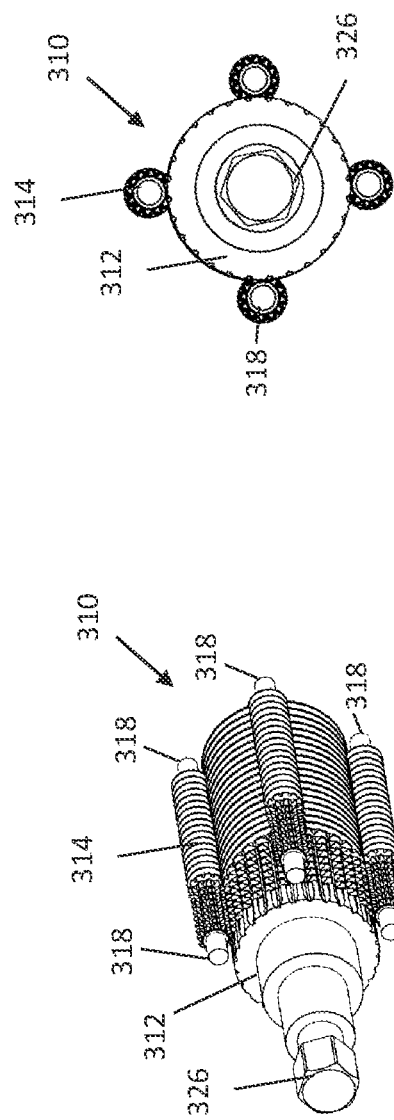

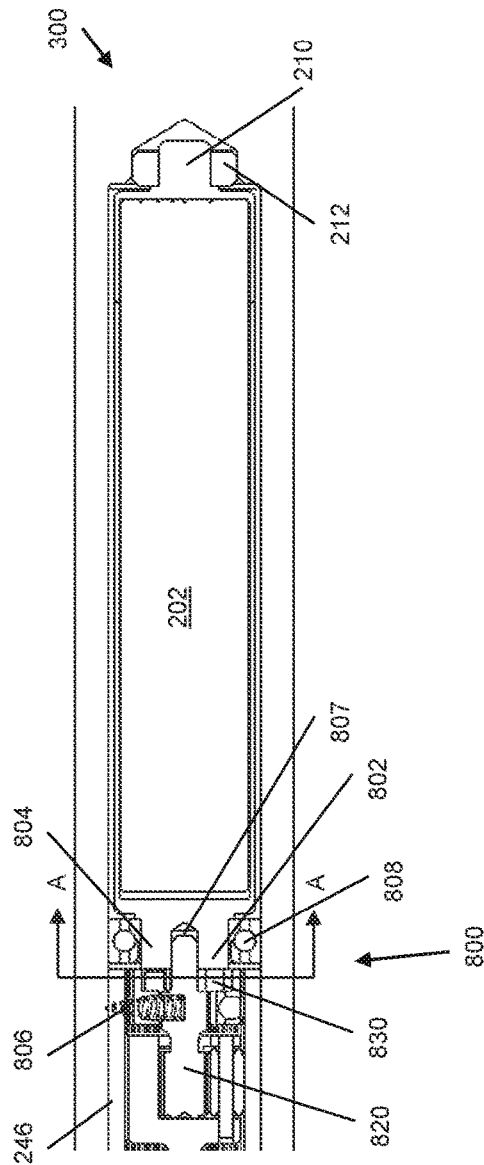
FIG. 28
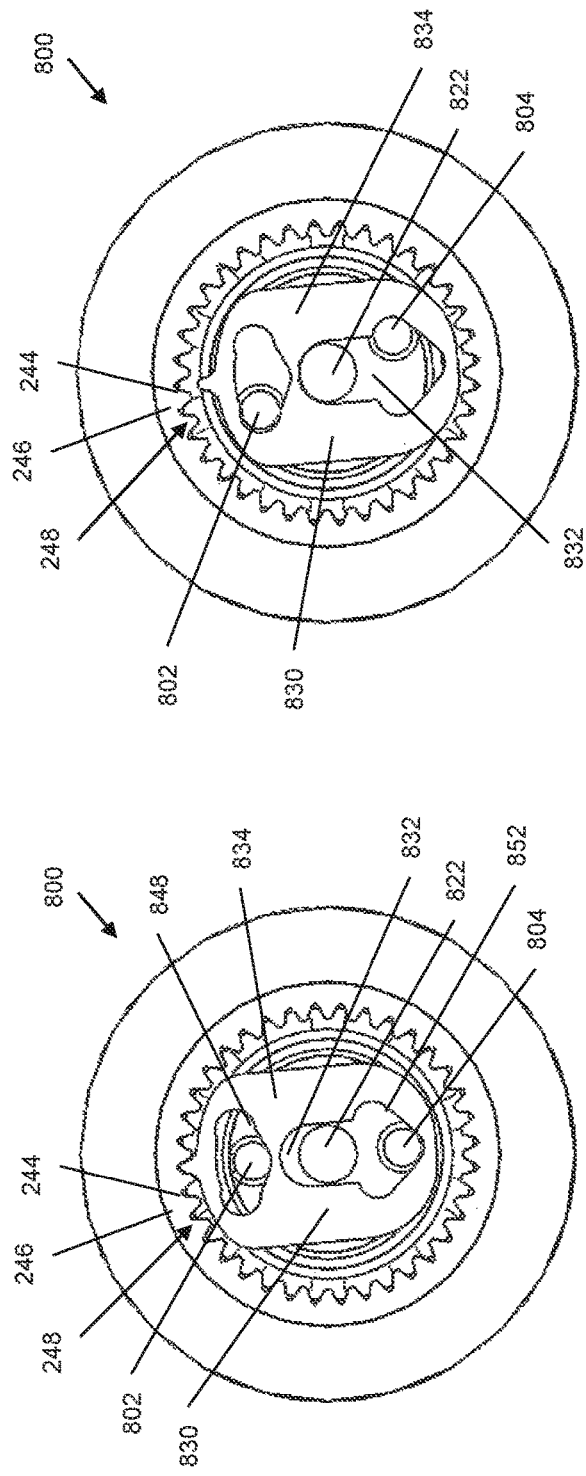
FIG. 30
FIG. 29

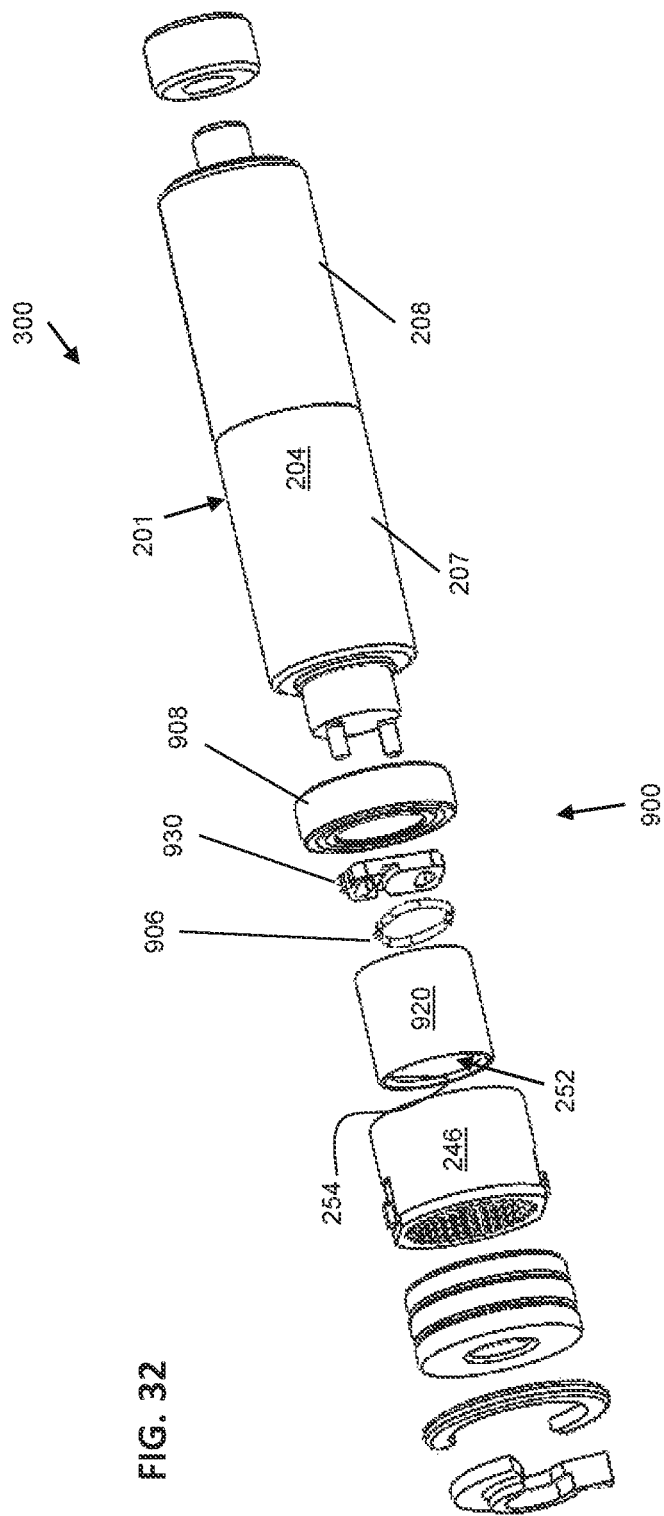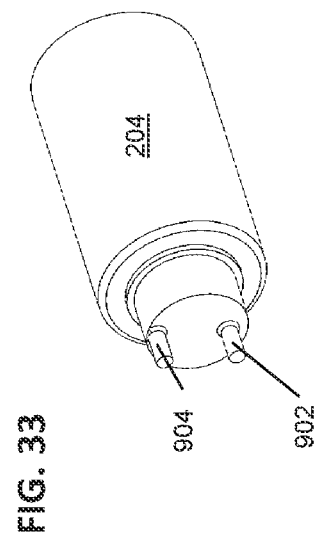

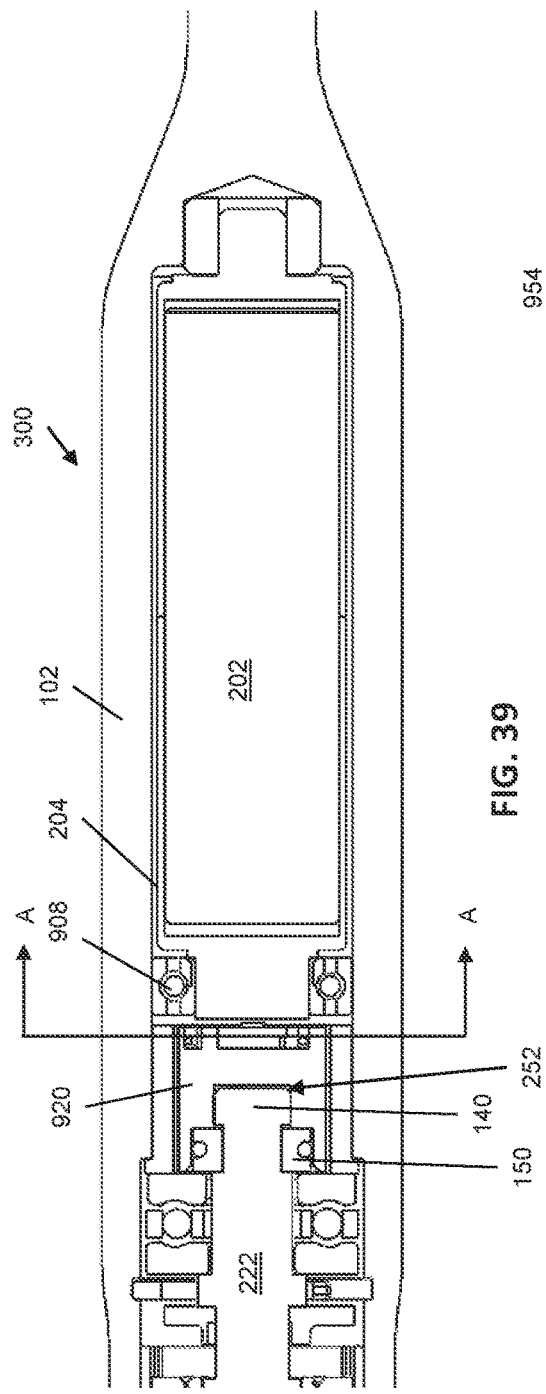
FIG. 39
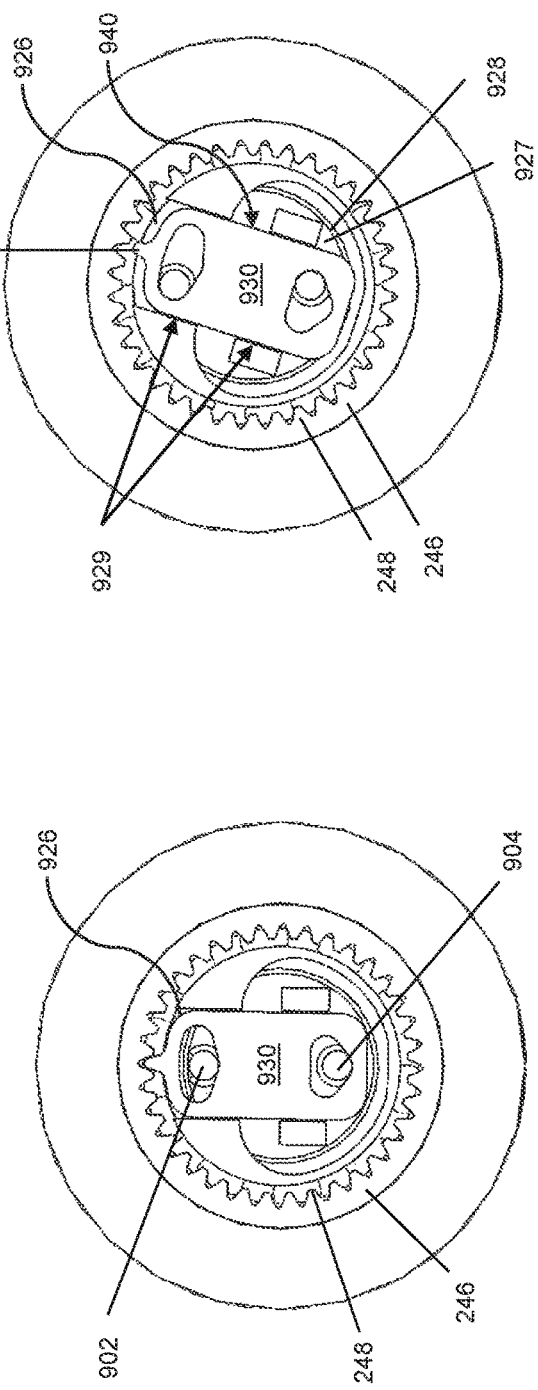
FIG. 41
FIG. 40

ADJUSTABLE IMPLANT

CROSS REFERENCE TO RELATED APPLICATION

The present patent application claims priority to U.S. Provisional Patent Application No. 63/229,014, filed on Aug. 3, 2021. The foregoing application is incorporated by reference as though fully set forth herein.

TECHNICAL FIELD

The subject matter described herein relates to adjustable implants, including intramedullary distraction and compression devices and/or adjustable spinal rods.

BACKGROUND

Distraction osteogenesis is a technique which has been used to grow new bone in patients with a variety of defects. For example, limb lengthening is a technique in which the length of a bone, for example a femur or tibia, may be increased. By creating a corticotomy or osteotomy in the bone, which is a cut through the bone, the two resulting sections of bone may be moved apart at a particular rate, such as one (1.0) mm per day, allowing new bone to regenerate between the two sections as they move apart. This technique of limb lengthening may be used in cases where one limb is longer than the other, such as in a patient whose prior bone break did not heal correctly, or in a patient whose growth plate was diseased or damaged prior to maturity. In some patients, stature lengthening is desired, and is achieved by lengthening both femurs and/or both tibias to increase the patient's height.

Limb lengthening is often performed using external fixation, wherein an external distraction frame is attached to the two sections of bone by pins which pass through the skin. The pins can be sites for infection and are often painful for the patient, as the pin placement site or "pin tract" remains a somewhat open wound throughout the treatment process. The external fixation frames are also bulky, making it difficult for patient to comfortably sit, sleep, and move. Intramedullary lengthening devices also exist, such as those described in U.S. Patent Application Publication No. 2011/0060336, which is incorporated by reference herein.

SUMMARY

A first aspect of the disclosure provides an adjustable implant including a housing having an internal thread and defining a cavity within the housing; a first adjustable member at least partially positioned within the housing and moveable relative to the housing within the cavity; and a first actuation assembly positioned within the first adjustable member and configured to move the first adjustable member relative to the housing. The first actuation assembly includes: an actuator configured to be activated by an external adjustment device; a gear assembly coupled to the actuator; an output driver coupled to the gear assembly; and a nut disposed at least partially surrounding the output driver and having an outer thread configured to communicate with the internal thread of the housing.

A second aspect of the disclosure provides an adjustable implant comprising a housing defining a cavity; a first adjustable member at least partially positioned within the housing and moveable relative to the housing within the cavity; and a first actuation assembly positioned within the first adjustable member and configured to move the first adjustable member relative to the housing. The first actuation assembly includes: an actuator configured to be activated by an external adjustment device; a gear assembly coupled to the actuator; a roller driver coupled with the gear assembly; at least one threaded roller positioned radially about and threadingly engaged with both the roller driver and an internal thread of the housing; and a cage substantially surrounding the roller driver and defining at least one aperture configured to receive the at least one threaded roller therein.

BRIEF DESCRIPTION OF THE DRAWINGS

The accompanying drawings, which are incorporated in and constitute a part of this specification, show certain aspects of the subject matter disclosed herein and, together with the description, help explain some of the principles associated with the disclosed implementations. In the drawings.

FIG. 4 shows an exploded perspective view of a nut, an output driver, and drive shaft according to embodiments of the disclosure;

FIG. 5 shows a cross-sectional view taken at box B of FIG. 2;

FIG. 6 shows a perspective view of an anti-jam feature according to embodiments of the disclosure;

FIG. 10 shows a front perspective view of a roller screw according to embodiments of the disclosure;

FIG. 11 shows a rear perspective view of a roller screw according to embodiments of the disclosure;

FIG. 12 shows a front perspective view of the roller screw with the cage removed according to embodiments of the disclosure;

FIG. 13 shows a front view of the roller screw according to the embodiment shown in FIG. 12 with the cage removed;

FIG. 28 shows a cross sectional view of a portion of an exemplary distraction and compression device including a lock mechanism in accordance with an embodiment of the disclosure;

FIGS. 29 and 30 show cross-sectional views taken along line A-A of FIG. 28, in which FIG. 29 depicts the locked position and FIG. 30 depicts the unlocked position, in accordance with embodiments of the disclosure;

FIG. 32 shows an exploded perspective view of a magnet assembly and a magnet lock mechanism in accordance with an embodiment of the disclosure;

FIG. 33 shows an enlarged perspective view of the magnet housing of FIG. 32, in accordance with an embodiment of the disclosure;

FIG. 39 shows a cross sectional view of a portion of an exemplary distraction and compression device including a lock mechanism in accordance with an embodiment of the disclosure;

FIGS. 40 and 41 show cross-sectional views taken along line A-A of FIG. 39, in which FIG. 40 depicts the locked position and FIG. 41 depicts the unlocked position, in accordance with embodiments of the disclosure;

Figure 1:
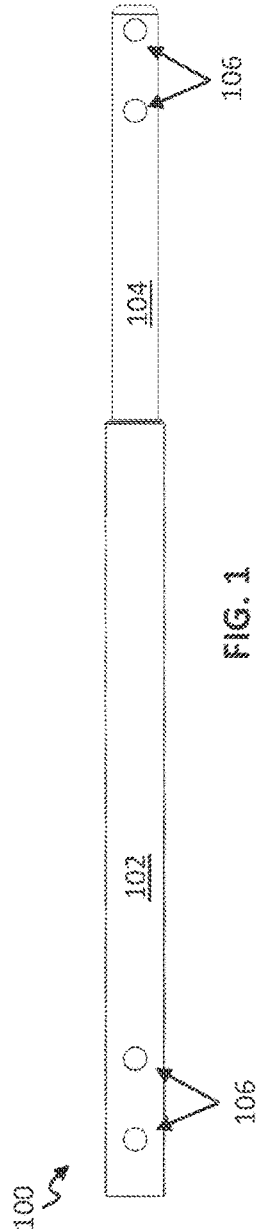
FIG. 1 shows a top view of an adjustable implant according to an embodiment of the disclosure.

It is noted that the drawings of the subject matter are not necessarily to scale. The drawings are intended to depict only typical aspects of the subject matter, and therefore, should not be considered as limiting the scope of the disclosed subject matter. In the drawings, like numbering represents like elements between the drawings.

DETAILED DESCRIPTION

The present disclosure describes various embodiments of an adjustable implant, such embodiments including intramedullary distraction and compression devices and/or adjustable spinal rods. The adjustable implant is configured to be externally controlled by an external adjustment device, and is therefore non-invasively adjustable. The adjustable implant includes a housing; a first adjustable member at least partially positioned within the housing and moveable relative to the housing; and a first actuation assembly positioned within the first adjustable member and configured to move the first adjustable member relative to the housing. In some embodiments, the actuation assembly includes a gear assembly. In other embodiments, the actuation assembly includes a roller screw assembly. In yet another embodiment, the actuation assembly includes an output driver coupled to a magnetic assembly. Positioning the actuation assembly within the adjustable portion facilitates making the adjustable implant smaller overall.

Figure 2:
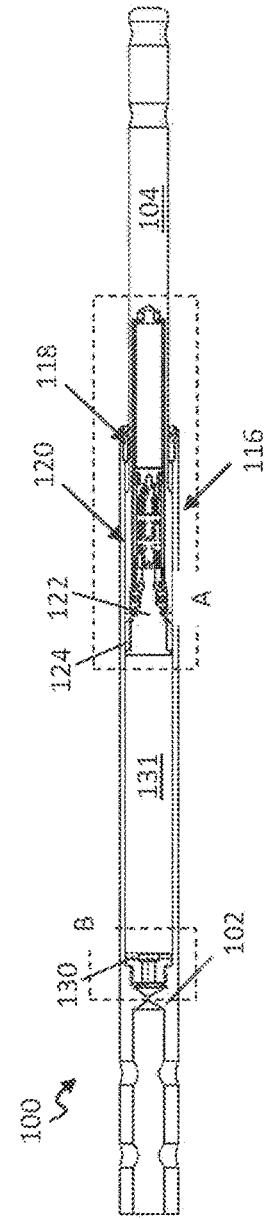
FIG. 2 shows a cross-sectional view of the adjustable implant of FIG. 1.

FIGS. 1-2 show an adjustable implant 100 according to a first embodiment. In this embodiment, the adjustable implant 100 includes a housing 102 and an adjustable member 104. The adjustable member 104 is at least partially disposed within the housing 102 and is moveable relative to the housing 102. As shown, each of the housing 102 and adjustable member 104 can include one or more fixation apertures 106 for receiving fixation elements, e.g., bone screws, therein for affixing the housing 102 and the adjustable member 104 to respective sections of bone.

The housing 102 is configured to be affixed to a bone at a first location, and the adjustable member 104 is configured to be affixed to the bone at a second location. The first and second locations may be disposed on separate sections of the same bone, or on separate bones, e.g., in the case of a spinal rod. In order to grow or lengthen the bone, the bone either has a pre-existing separation or is purposely cut or broken (e.g., via an osteotomy) to create this separation, dividing the bone into a first section and a second section. The cut may be done prior to implanting and securing the adjustable implant 100 or may be done after the adjustable implant 100 is implanted, for example by use of a flexible Gigli saw. As will be described herein, the adjustable member 104 is configured to contract (e.g., for compression) and/or distract (e.g., for limb lengthening) relative to the housing 102. The adjustable implant 100 is configured to provide controlled, precise translation of the adjustable member 104 relative to the housing 102 by non-invasive remote control, and thus provide controlled, precise translation of the bone segment that is secured to the adjustable member 104 relative to the bone segment that is secured to the housing 102.

Over the treatment period for limb lengthening, the bone is regularly distracted, creating a new separation, into which osteogenesis can occur. "Regularly distracted" is meant to indicate that distraction occurs on a regular or periodic basis which may be on the order of every day or every few days. An exemplary distraction rate is one millimeter per day, although, other distraction rates may be employed. That is to say, a typical distraction regimen may include a daily increase in the length of the adjustable implant 100 by about one millimeter. This may be done, for example, by four lengthening periods per day, each having 0.25 mm of lengthening. The adjustable implant 100, as disclosed in more detail below, may include a magnetic drive system, which causes the adjustable member 104 to telescopically extend from the housing 102, thus forcing the first section and the second section of the bone apart from one another.

Figure 3:
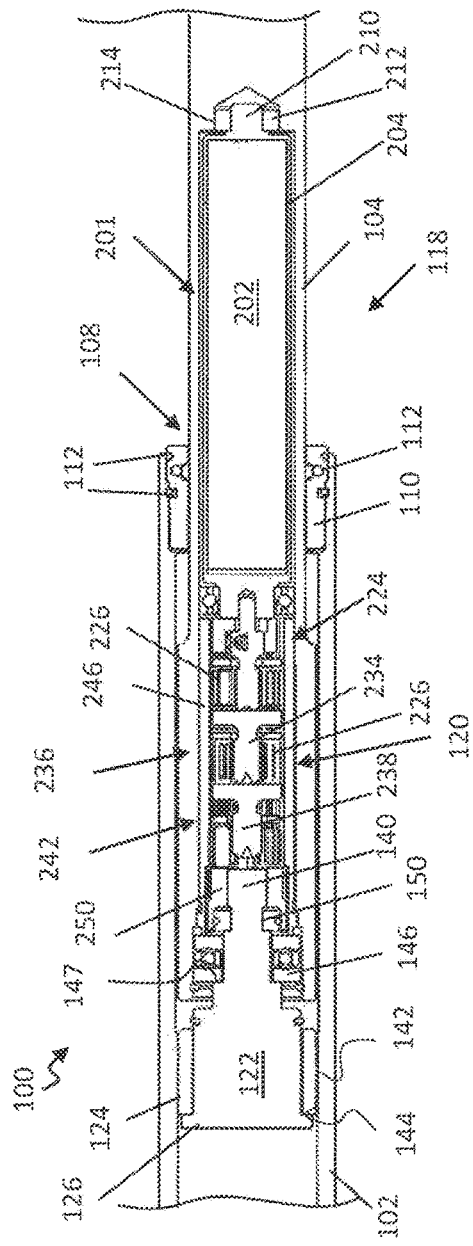
FIG. 3 shows an enlarged cross-sectional view of the adjustable implant taken at box A of FIG. 2.

Turning to FIG. 3, at one end, the housing 102 has an opening 108 for receiving the adjustable member 104. One or more o-rings, radial seals, or retainers can be positioned about the adjustable member 104 between the adjustable member 104 and the housing 102. In some embodiments, an intermediary member 110 is positioned between the housing 102 and the adjustable member 104. The intermediary member 110 provides for improved sealing and/or retention. Specifically, the intermediary member 110 can provide an anti-rotation mechanism that prevents rotation of the adjustable member 104 relative to the housing 102. For example, an outer geometry of the adjustable member 104 and an inner geometry of the intermediary member 110 may complement and matingly engage one another. For example, the adjustable member 104 may have a cross sectional geometry that is oblong, elliptical, etc., and the opening 108 of the housing 102 may have a cross sectional geometry that is complementary to that of the adjustable member 104 and is therefore also oblong, elliptical, etc. In some embodiments, an outer cross sectional geometry of the adjustable member 104 and an inner cross sectional geometry of the intermediary member 110 may include one or more flat surfaces configured to matingly engage one another. The intermediary member 110 may include at least one groove facing an outer surface of the adjustable member 104 and at least one groove facing an inner surface of the housing 102. A first radial seal, o-ring, or retainer 112 may be positioned within the at least one groove facing the outer surface of the adjustable member 104. A second radial seal, o-ring, or retainer 112 may be positioned within the at least one groove facing the inner surface of the housing 102. In some embodiments, a portion of the outer surface of the adjustable member 104 and/or a portion of an internal surface of the housing 102 can be recessed to accommodate the first and/or second radial seals, o-rings, or retainers 112. That is, the outer surface of the adjustable member 104 and/or a portion of an internal surface of the housing 102 can include complementary grooves facing the grooves formed within the intermediary member 110 for receiving the radial seals, o-rings, or retainers 112 therein. The intermediary member 110, including the radial seals, o-rings, or retainers 112 can help facilitate proper sealing between the housing 102 and the adjustable member 104 so that bodily fluid does not enter the housing 102 when the adjustable implant 100 is implanted. It is to be understood that any combination of radial seals, o-rings, or retainers 112 can be used within the intermediary member 110 without departing from aspects of the disclosure. Further, any of the sealing or retention features described in International Patent Application No. PCT/US2022/031709, filed on Jun. 1, 2022, can also be used without departing from aspects of the disclosure. International Patent Application No. PCT/US2022/031709 is hereby incorporated by reference in its entirety as if set forth herein.

Turning to FIGS. 2 and 3, the adjustable implant 100 also includes an actuation assembly 116 positioned within the adjustable member 104 and configured to move the adjustable member 104 relative to the housing 102. The adjustable member 104 is configured to move within a cavity 131 of the housing 102. The actuation assembly 116 includes an actuator 118 configured to be activated by an external adjustment device 400 (see FIGS. 42-44), a gear assembly 120 coupled to the actuator 118, an output driver 122 coupled to the gear assembly 120, and a nut 124 disposed at least partially surrounding the output driver 122. The gear assembly 120 can include at least one stage of planetary gears. The embodiment illustrated in FIG. 3 includes three stages of gears, including first stage 224, second stage 236, and third stage 242, as discussed further herein. The nut 124 may include an outer thread 142 (shown in detail in FIG. 4) configured to communicate with an inner thread 144 of the housing 102.

With continued reference to FIG. 3, the actuator 118 includes a rotatable magnetic assembly 201 that is located within the adjustable member 104. The magnetic assembly 201 includes a cylindrical, radially-poled permanent magnet 202 contained within a magnet housing 204. The permanent magnet 202 may include rare earth magnet materials, such as Neodymium-Iron-Boron. The permanent magnet 202 has a protective Phenolic coating and may be held statically within the magnet housing 204 by epoxy or other adhesive. The magnet housing 204 and epoxy form a seal to further protect the permanent magnet 202. The magnet housing 204 may also be welded to create a hermetic seal. To aid in manufacturing and assembly, the magnet housing 204 may include separate magnet cups 207, 208 (see FIGS. 21 and 32) for housing the permanent magnet 202 therein. One end of the magnet housing 204 includes a cylindrical extension or axle 210 which fits within the inner diameter of a radial bearing 212, allowing for low friction rotation. The outer diameter of the radial bearing 212 fits within cavity of a maintenance member 214.

Figure 42:
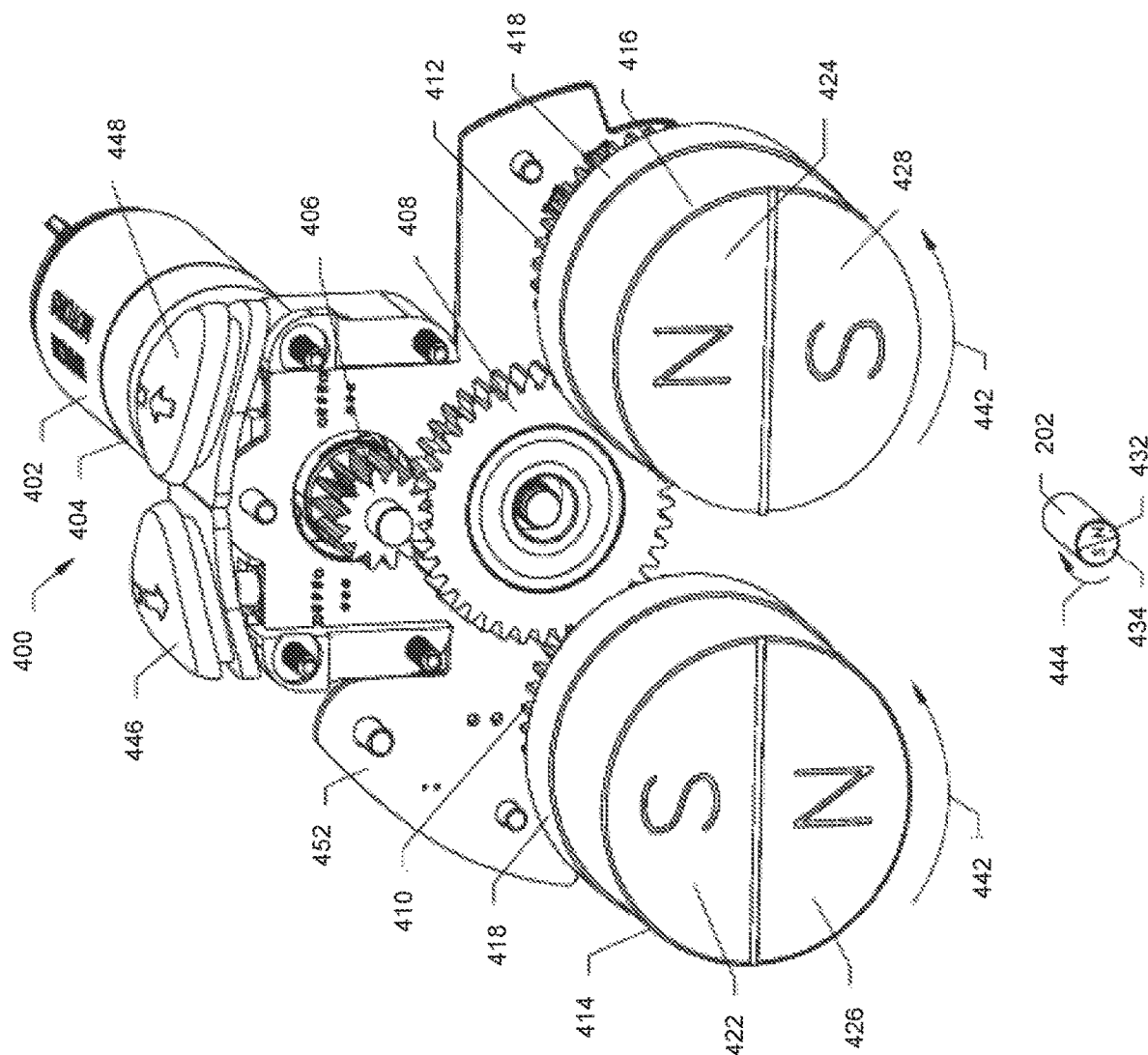
FIG. 42 shows internal components of an external adjustment device for non-invasively adjusting an adjustable implant according to embodiments of the disclosure.
Figure 43:
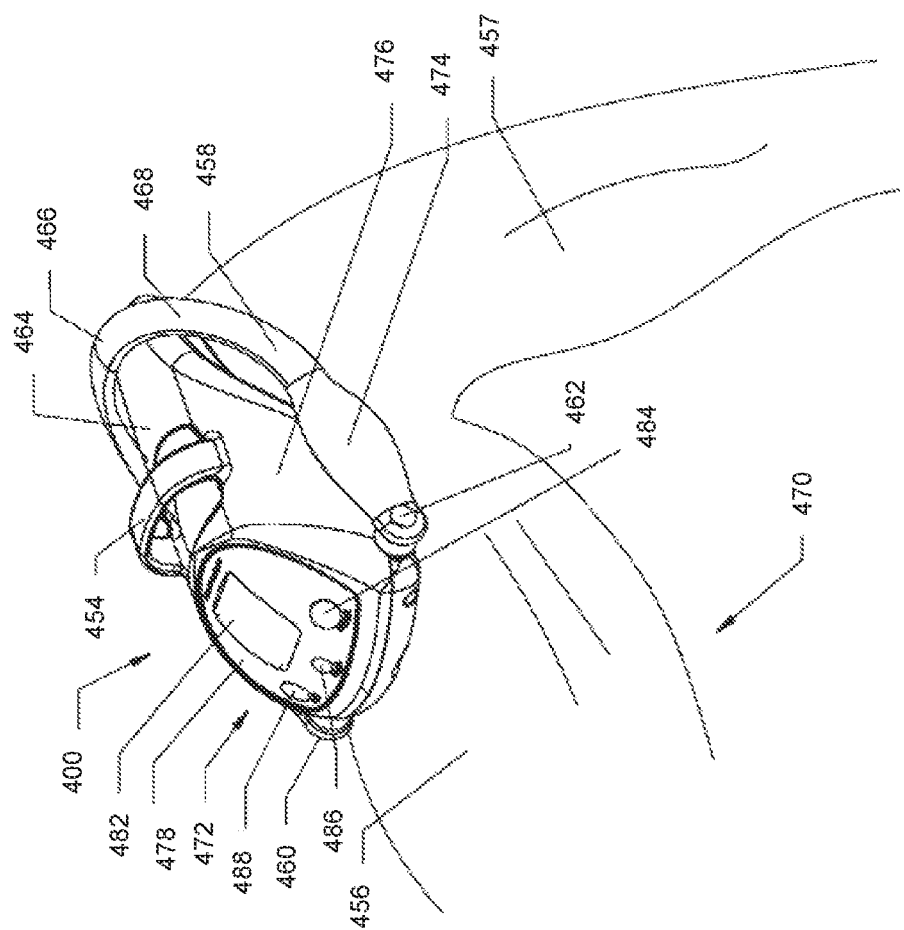
FIG. 43 shows an external adjustment device in a configuration for adjusting an adjustable implant according to embodiments of the disclosure implanted within the femur.
Figure 44:
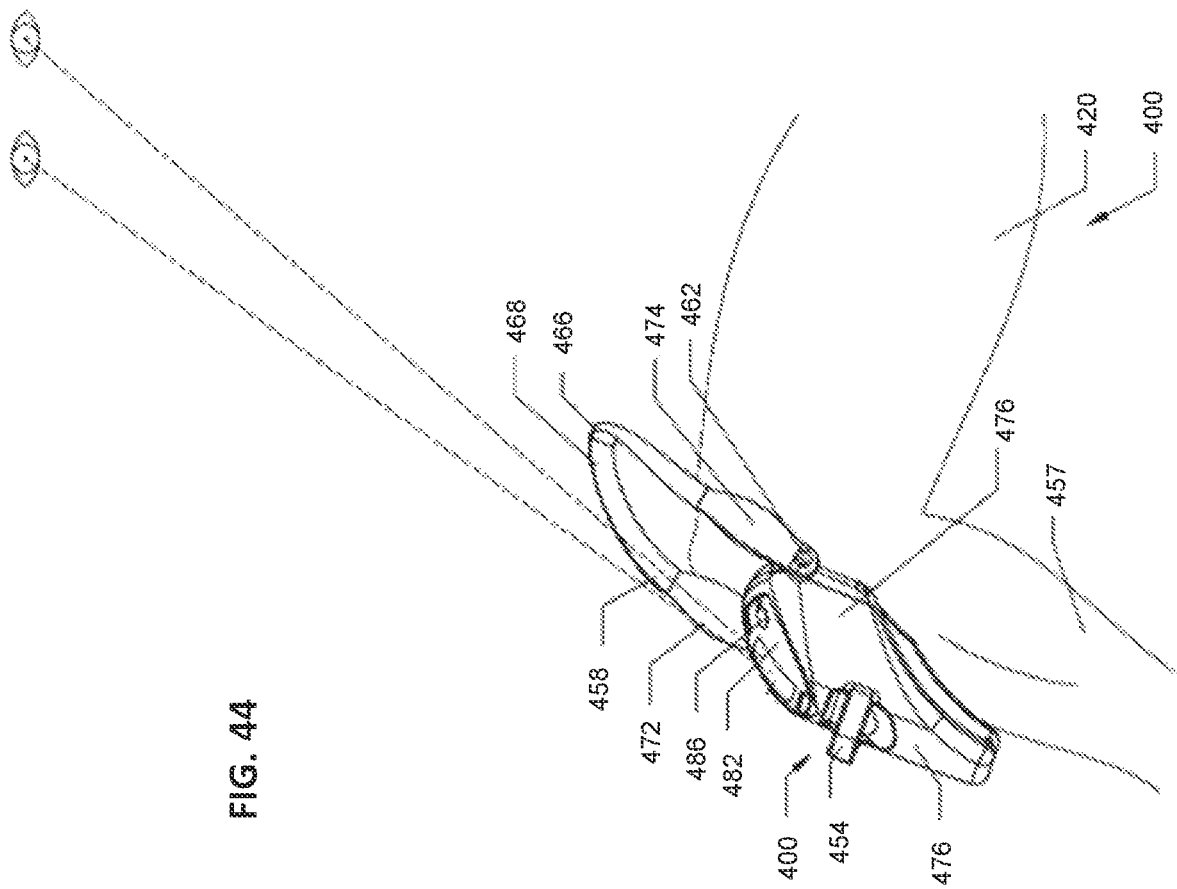
FIG. 44 shows an external adjustment device according to embodiments of the disclosure in a configuration for adjusting an adjustable implant implanted within the tibia.

The maintenance member 214 prevents the adjustable implant 100 from being accidentally adjusted by movements of the patient. The maintenance member 214 is positioned proximate and axially spaced from the magnetic assembly 201 within the adjustable implant 100. The maintenance member 214 may be made from a magnetically permeable material, such as 400 series stainless steel. The maintenance member 214 may be configured to maintain a position of the magnetic assembly 201 in the absence of the rotating magnetic field. When the adjustable implant 100 is not being adjusted (e.g., using an external adjustment device 400 as shown in FIGS. 42-44), the magnetic poles of the radially-poled cylindrical magnet 202 are magnetically attracted by the maintenance member 214. However, when the magnetic assembly 201 is forced to rotate due to the effect of a sufficiently large rotating magnetic field on the radially-poled cylindrical magnet 202, the magnetic assembly 201 overcomes the relatively weaker attractions of the maintenance member 214. Additional details of the maintenance member can be found in U.S. Pat. Pub. 20190015138, published Jan. 17, 2019, which is incorporated herein by reference as if set forth in its entirety. Other maintenance members may also be used, such as those disclosed in International Patent App. Pub. No. WO 2022/015898 A1, published Jan. 20, 2022; U.S. Pat. No. 8,734,488, published May 27, 2014; and U.S. Pat. Pub. 20130338714, published Dec. 19, 2013, each of which are incorporated herein by reference as if set forth in its entirety.

The magnetic assembly 201 is coupled to the gear assembly 120 at a first, input end of the gear assembly 120. The gear assembly 120 is configured to couple at an opposite, output end thereof to the output driver 122, thereby coupling the magnetic assembly 201 to the output driver 122. Referring to FIG. 3, at the end opposite the axle 210, the magnetic assembly 201 terminates in a first sun gear 218, which may be integral to the magnet housing 204. The first sun gear 218 may also be made as a separate component and secured to the magnet housing 204, for example by welding. The first sun gear 218 turns with rotation of magnetic assembly 201 (in a 1:1 fashion) upon application of a moving magnetic field applied to the patient from an external location. The first sun gear 218 is configured to insert within an opening of a first gear stage 224, the first gear stage 224 including a plurality of planetary gears 226, e.g., three planetary gears 226, which are rotatably held in a frame 228 by axles 232 (visible in FIG. 21). A second sun gear 234, which is the output of the first gear stage 224, turns with the frame 228 of the first gear stage 224. The identical components exist in a second gear stage 236, which outputs to a third sun gear 238, and a third gear stage 242, which terminates in a drive stage 250. The drive stage 250 is positioned at the end of gear assembly 120 furthest from the magnet assembly 201. Along the length that the gear stages 224, 236, 242 extend, the inner wall 244 of a ring gear 246 has internal teeth 248 along which the externally extending teeth of the planetary gears 226 engage (illustrated in, e.g., FIGS. 21 and 28-30), as they turn. Each gear stage 224, 236, 242 illustrated has a 4:1 gear ratio, so the drive stage 250 turns once for every 64 turns of the magnetic assembly 201.

The frame of the third gear stage 242 includes the drive stage 250. Turning to FIG. 4, the drive stage 250 includes an opening 252 having a keyed internal surface 254. The keyed internal surface 254 is configured to matingly engage a keyed external surface 140 of the end of the output driver 122. The engagement of the keyed surfaces 254, 140 prevent rotation of output driver 122 and the drive stage 250 relative to each other. The keyed surfaces 254, 140 may be, for example, a hex shape. However, other shapes that prevent rotation of the output driver 122 relative to the drive stage 250 are also contemplated by the disclosure. To further maintain the output driver 122 within the drive stage 250, a first retainer clip 150 (FIG. 3) may be provided within the opening 252 of the drive stage 250 and at least partially surrounding the output driver 122 proximal to the keyed external surface 140. Specifically, the retainer clip 150 is positioned about a recessed or smaller diameter portion within the opening 252.

As discussed above, the torque applied on the magnetic assembly 201 by the action of the rotating magnetic field on the cylindrical permanent magnet 202, is augmented on the order of 64 times in terms of the turning torque of the output driver 122. This allows the adjustable member 104 to be able to move with high precision. Because of the 64:1 gear ratio, the adjustable implant 100 is able to axially displace the bone segment coupled to the adjustable member 104 against severe resisting forces, for example those created by soft tissue.

Referring back to FIG. 3, one or more thrust bearing(s) 146 may also be provided within the adjustable implant 100. In some embodiments, a thrust bearing 146 is positioned about at least a portion of the output driver 122 within the adjustable member 104. The thrust bearings 146 serve to protect the magnetic assembly 201 and the gear assembly 120 of the drive system from any significant compressive or tensile stresses. When there is a compressive force on the implant 100, for example, when distracting a bone, and thus resisting the tensile strength of the soft tissues, the thrust bearing(s) 146 abut against the retainer clip(s) 150 and/or a ledge 147.

Additionally, in certain compressive applications it is the goal to hold two fractured sections of a bone together. Because the bone may have fractured in a non-uniform or shattered pattern, it may be difficult to determine the desired length of the adjustable implant 100 until after it is implanted and fully attached. In these situations, it may be preferred to place a slightly extended adjustable implant 100, secure the implant 100, and then magnetically retract the adjustable implant 100 after it has been secured within the bone fragments. In this manner, the implant 100 may apply the desired compression between the two fragments. In such compressive applications, the adjustable implant 100 is under tensile forces and the thrust bearing(s) 146 would abut against the retainer clip(s) 150 or a ledge 147. In both situations, the thrust bearings 146 and the ledge 147 take the large stresses, rather than the magnetic assembly 201 or gear assembly 120 of the drive system.

As shown in FIGS. 3 and 4, the output driver 122 may include a flanged portion 126 on an end opposite the keyed portion 140. The flanged portion 126 is configured to abut the nut 124 and maintain a position of the nut 124 relative to the output driver 122. The output driver 122 also includes a tab 128 (FIG. 4) extending from the flanged portion 126. The tab 128 is configured to interact with an anti-jam feature 130 (FIGS. 2 and 5-6). The anti-jam feature 130 is configured to prevent the adjustable member 104 from jamming or stalling in a fully retracted state. Specifically, the anti-jam feature 130 provides a spring force adapted to overcome a friction force of the adjustable member 104 in a scenario where the adjustable member 104 jams or stalls. The anti-jam feature 130 is positioned within the cavity 131 on an opposite end of the opening 118 that receives the adjustable member 104. The anti-jam feature 130 includes a spring tab 132. The tab 128 of the output driver 122 complements the spring tab 132 and is configured to matingly engage the spring tab 132 when the adjustable implant 100 is in the fully retracted state. The spring tab 132 is configured to provide a spring force upon the output driver 122 when the adjustable implant 100 is in the fully retracted state to prevent the output driver 122 from jamming or becoming stuck in the fully retracted state within the housing 102. As shown in FIG. 6, the anti-jam feature 130 includes a threaded portion 134 configured to thread within the cavity 131 of the housing 102 (FIG. 5) so that the anti-jam feature 130 does not rotate relative to the housing 102 once in place. The anti-jam feature 130 also includes a substantially annular collar 136 having a slit 138 disposed on a radially outward facing surface of the collar 136. The slit 138 may extend through a portion of the collar 136, forming a spring portion 139. The spring portion 139 may be axially separated from the remaining portion of the collar 136 by the slit 138. The spring tab 132 is positioned on the spring portion 139 on an end face of the collar 136 that is opposite the threaded portion 134.

Together, the anti-jam feature 130 and tab 128 of the output driver 122 prevent the adjustable member 104 from jamming or stalling in a fully retracted state. For example, an adjustable member 104 may become jammed in a fully retracted state due to frictional forces in the retracted state. Therefore, a torque greater than a torque provided by the external adjustment device 400 (FIGS. 42-44) may be needed to jumpstart or overcome the frictional forces in a jammed state. As a result, the anti-jam feature 130 provides a built-in mechanism within the adjustable implant 100 to provide an additional force above and beyond that which is provided by the external adjustment device 400 thereby providing such a jump start force. Specifically, in a jammed state, the external adjustment device 400 causes the magnetic assembly 201, and therefore the output driver 122 to rotate, but the adjustable member 104 may not move axially due to being jammed. In the jammed state, the tab 128 engages with the spring tab 132 of the anti-jam feature 130. This causes the spring portion 139 to bias toward the portion of the collar 136, across the slit 138. As the external adjustment device 400 causes the output driver 122 to rotate, and with the spring portion 139 in a compressed position biased toward the remainder of the collar 136, the spring portion 139 springs away from the remainder of the collar 136 and toward the output driver 122. The output driver 122 maintains contact with the anti-jam feature 130, thereby providing sufficient force to overcome the frictional forces holding the adjustable portion 104 in the jammed state. As a result, this causes the adjustable portion 104 to become unjammed.

Returning to FIG. 3, upon actuation of the actuator 118 by the external adjustment device 400 (FIGS. 42-44), the outer thread 142 of the nut 124 is configured to interact with the internal thread 144 of the housing 102 to cause the adjustable member 104 to move relative housing 102. More specifically, actuation of the actuator 118 by the external adjustment device 400 causes the actuator 118 to rotate which in turn causes the gear assembly 120 to rotate which in turn causes the output driver 122 and nut 124 to rotate.

As shown in the embodiment of FIG. 4, the output driver 122 may include at least one flat outer surface 129, and the nut 124 may include at least one corresponding flat interior surface 125 configured to engage that at least one flat outer surface 129 of the output driver 122. This configuration prevents the output driver 122 from rotating relative to the nut 124. Therefore, as the output driver 122 rotates, the nut 124 rotates. Rotation of the cylindrical permanent magnet 202, which is magnetically driven by an external adjustment device 400 (FIG. 42), effectuates rotation of the output driver 122 and the nut 124. Rotation of the output driver 122 and nut 124 then translates into axial movement of the adjustable member 104 relative to the housing 102 due to the threaded interaction between the nut 124 and the housing 102.

Figure 7:
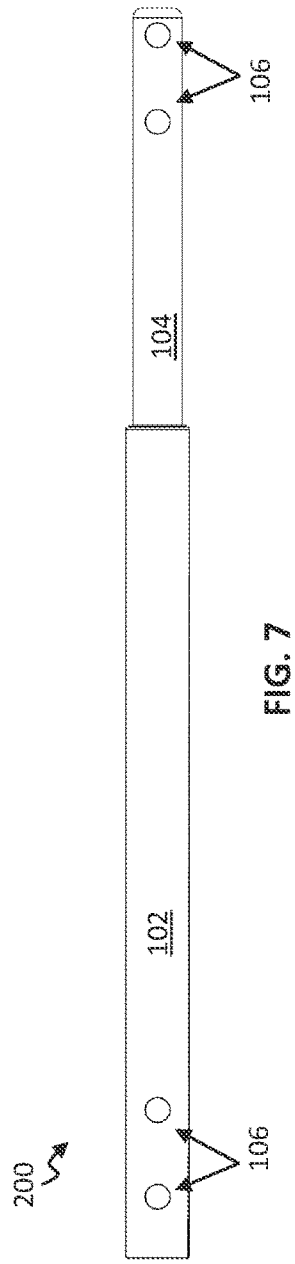
FIG. 7 shows a top view of an adjustable implant according to an embodiment of the disclosure.
Figure 8:
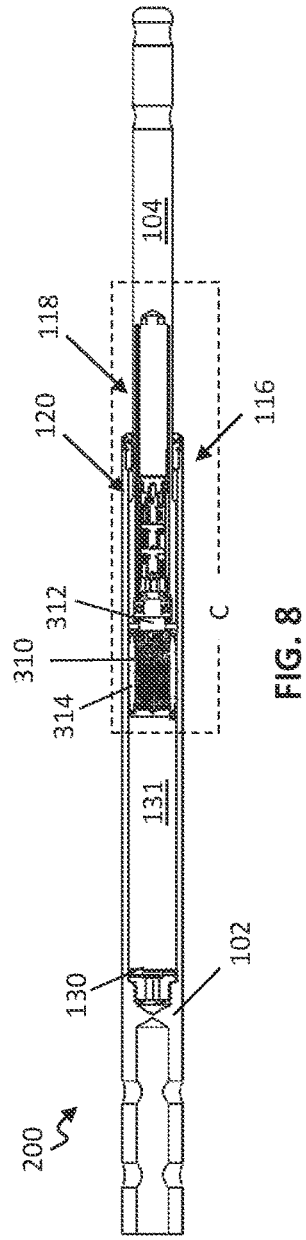
FIG. 8 shows a cross-section view of the adjustable implant of FIG. 7.
Figure 9:
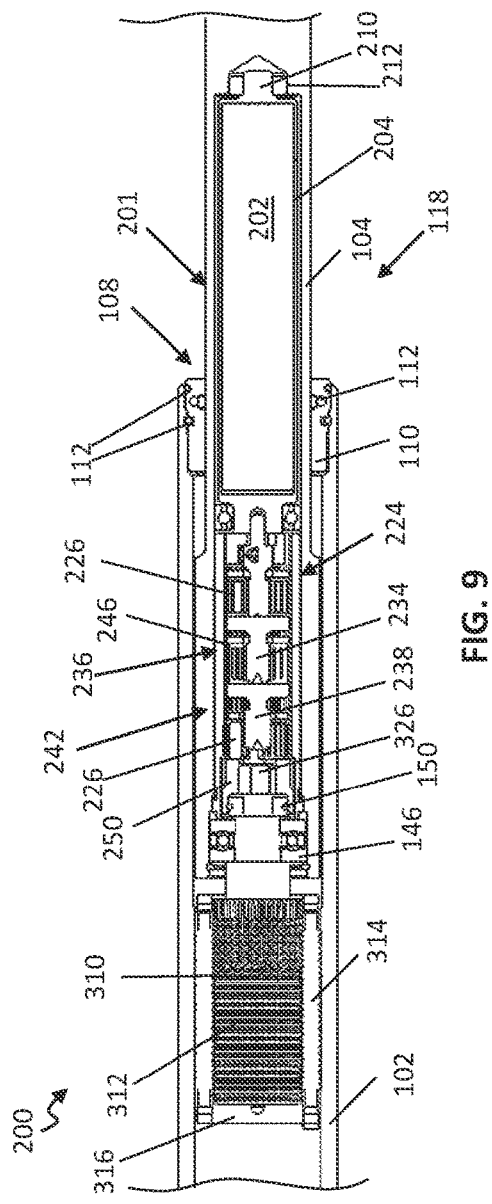
FIG. 9 shows an enlarged cross-sectional view of the adjustable implant taken at box C of FIG. 8.

Turning to FIGS. 7-9, another embodiment of an adjustable implant 200 is shown. The adjustable implant 200 is substantially the same as adjustable implant 100, and therefore, like numbering represents the same components, and description of which is not repeated herein for brevity. The adjustable implant 200 differs from the adjustable implant 100 in that the actuation assembly 116 includes an inverted roller screw 310 (FIGS. 9-13) instead of the output driver 122 and nut 124 of adjustable implant 100. The inverted roller screw 310 reduces friction, thereby making the adjustable implant more efficient in friction losses overall.

More specifically, the actuation assembly 116 according to this embodiment includes an actuator 118 configured to be activated by an external adjustment device 400, a gear assembly 120 coupled to the actuator 118, a roller driver 312 coupled with the gear assembly 120, at least one threaded roller 314 positioned radially about and threadingly engaged with the roller driver 312, and a cage 316 substantially surrounding the roller driver 312. The actuator 118 and gear assembly 120 are identical to that described previously herein, and therefore, repetitive description of which has been excluded for brevity.

The cage 316 includes at least one axially extending aperture 322 that is configured to receive the at least one threaded roller 314 therein. In some embodiments, the roller driver 312 includes four threaded rollers 314 positioned about 90° apart from one another about the roller driver 312, as best shown in FIG. 13. In such embodiments, the cage 316 may include four axially extending apertures 322 positioned about 90° apart from one another about the roller driver 312 (FIGS. 10-11), where each of the apertures 322 is configured to receive a respective threaded roller 314 therein. However, it is to be understood that any number of threaded rollers 314 and corresponding apertures 322 can be included without departing from aspects of the disclosure, for example, one, two, three, four, five, six, seven, eight, or more threaded rollers 314 and corresponding apertures 322.

Each threaded roller 314 includes a bearing or tab 318 on each end which is configured to seat within a cutout or pocket 320 formed within the cage 316, proximate the at least one aperture 322. Each aperture 322 of the at least one aperture 322 extends through a full thickness of the cage 316, thereby allowing the respective threaded roller 314 to extend radially through the cage 316 to engage both the roller driver 312 and the housing 102. Each threaded roller 314 of the at least one threaded roller 314 is configured to extend through the respective aperture 322 in the cage 316 to engage an internal thread 144 of the housing 102.

Each of the at least one threaded roller 314 and the roller driver 312 can include portions having differing thread configurations. This allows the torque to be transmitted to the output driver 122 and the housing 102. For example, one of the thread configurations can be configured to mesh with and interact with the internal thread 144 of the housing 102. Another of the thread configurations can be configured to mesh with and interact with the roller 314.

Like the output driver 122 discussed above relative to implant 100 of FIGS. 2-4, the roller driver 312 of implant 200 (FIGS. 8-9 and others) includes a keyed portion 326 configured to be received within the opening 252 (FIG. 4) of the drive stage 250. The keyed internal surface 254 of the opening 252 is configured to matingly engage the keyed external surface 326 of the end of the roller driver 312 in the same manner as described with regard to the keyed external surface 140 of the end of the output driver 122 shown in FIGS. 2-4. The engagement of the keyed surfaces 254, 326 prevents rotation of roller driver 312 and the drive stage 250 relative to each other. The keyed surfaces 254, 326 may be, for example, a hex shape. However, other shapes that prevent rotation of the roller driver 312 relative to the drive stage 250 are also contemplated by the disclosure.

Additionally, like the output driver 122, the cage 316 of the inverted roller screw 310 may include a tab 328 positioned on an end thereof, as shown in FIG. 11. The tab 328 may be positioned on an end of the cage 316 that is opposite the keyed portion 326. The tab 328 (FIG. 11) is configured to interact with the anti-jam feature 130 (FIGS. 2, 5-6, and 8) in the same manner as described relative to the tab 128 (FIGS. 4 and 20) to prevent jamming and/or unjam the adjustable member 104 relative to the housing 102 as described herein.

Upon actuation of the actuator 118 by the external adjustment device 400, the actuator 118 (i.e., the rotating magnetic assembly 201) rotates, which in turn causes the gear assembly 120 to rotate. This in turn causes the roller driver 312 to rotate, thereby causing the at least one threaded roller 314 to also rotate. As the threaded roller(s) 314 rotate, the threaded roller(s) 314 are configured to interact with the internal thread 144 of the housing 102 to cause the adjustable member 104 to move relative to the housing 102.

Figure 14:
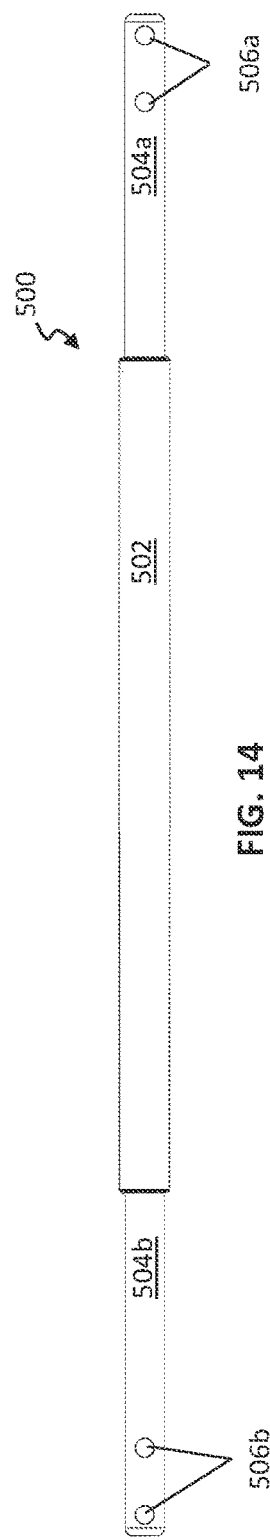
FIG. 14 shows a top view of an adjustable implant according to another embodiment of the disclosure.
Figure 15:
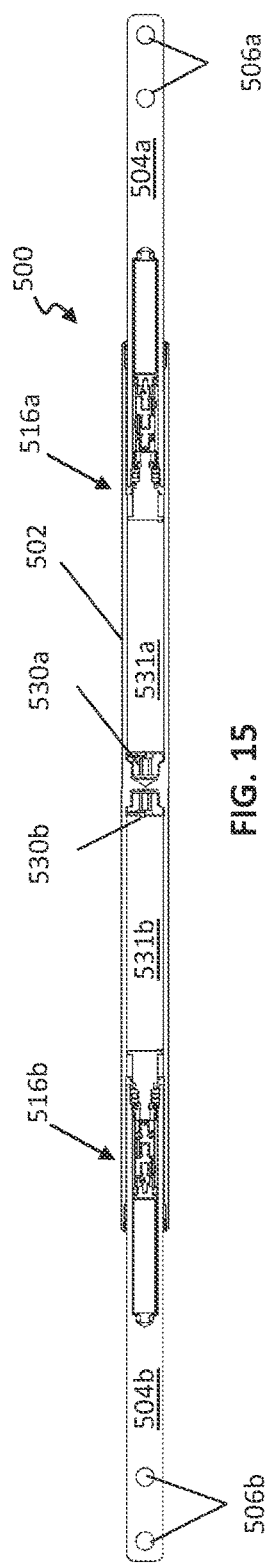
FIG. 15 shows a cross-sectional view of the adjustable implant of FIG. 14.

FIGS. 14 and 15 show another embodiment of an adjustable implant 500 according to aspects of the disclosure. In this embodiment, the adjustable implant 500 provides a dual rod adjustment implant that includes a mirrored configuration of adjustable implant 100. In this embodiment, the adjustable implant 500 includes a housing 502, a first adjustable member 504a and a second adjustable member 504b. The first adjustable member 504a is at least partially disposed within the housing 502 and is moveable, e.g. translatable, relative to the housing 502. The first adjustable member 504a includes at least one fixation aperture 506a configured to receive a fixation element therein to affix the first adjustable member 504a to bone. The second adjustable member 504b includes at least one fixation aperture 506b configured to receive a fixation element therein to affix the second adjustment member 504b to bone. In this embodiment, the housing 502 may include no fixation apertures. The second adjustment member 504b is at least partially disposed within the housing 502 and is moveable, e.g., translatable, relative to the housing 502. The first and second adjustable members 504a, 504b are positioned on opposing sides of the housing 502 relative to one another. That is, the second adjustable member 504b is positioned within an opposite end of the housing 502 relative to the first adjustable member 504a. The housing 502 includes two separate cavities 531a, 531b for receiving a respective adjustable member 504a, 504b therein. The adjustable implant 500 includes a first actuation assembly 516a configured to move the first adjustable member 504a relative to the housing 502, and a second actuation assembly 516b configured to move the second adjustable member 504b relative to the housing 502, such that each respective adjustable member 504a, 504b is individually controlled by its respective actuation assembly 516a, 516b. In this embodiment, the actuation assemblies 516a, 516b are substantially similar to the actuation assembly 116 of FIGS. 2-4. That is, the actuation assemblies 516a, 516b can each include an actuator 118 configured to be activated by an external adjustment device, a gear assembly 120 coupled to the actuator 118, an output driver 122 coupled to the gear assembly 120, and a nut 124 disposed at least partially surrounding the output driver 122. The nut 124 may include an outer thread 142 (FIG. 4) configured to communicate with an internal thread of the housing. The adjustable member 500 also includes a first anti-jam feature 530a and a second anti-jam feature 530b positioned within respective cavities 531a, 53 lb. The anti-jam features 530a, 530b are identical to the anti-jam feature 130 described herein (FIGS. 2, 5-6, and 8).

Figure 16:
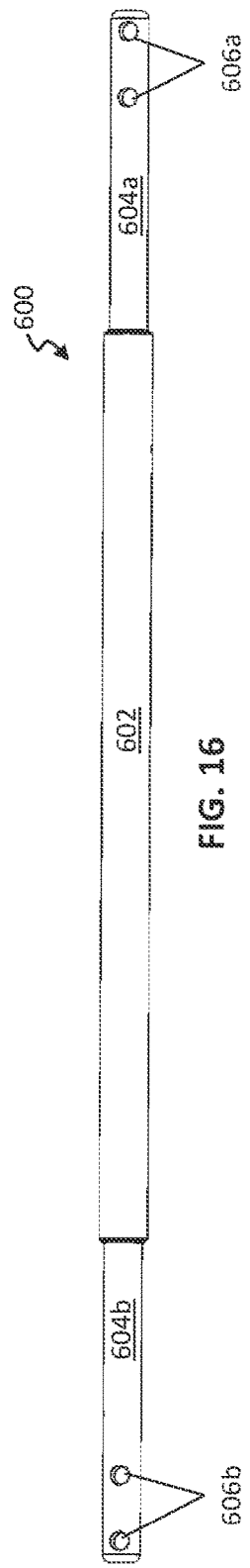
FIG. 16 shows a top view of an adjustable implant according to another embodiment of the disclosure.
Figure 17:
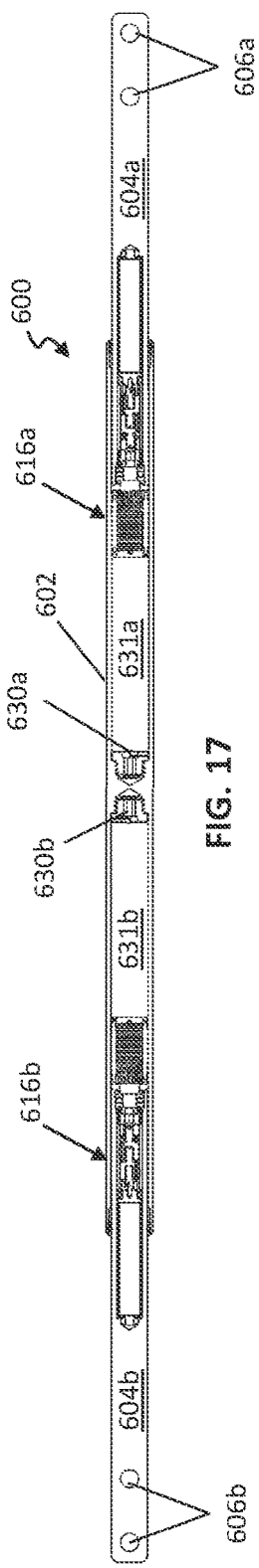
FIG. 17 shows a cross-sectional view of the adjustable implant of FIG. 16.

FIGS. 16 and 17 show another embodiment of an adjustable implant 600 according to aspects of the disclosure. In this embodiment, the adjustable implant 600 provides a dual rod adjustable implant that includes a mirrored configuration of the adjustable implant 200. In this embodiment, the adjustable implant 600 includes a housing 602, a first adjustable member 604a and a second adjustable member 604b. The first adjustable member 604a is at least partially disposed within the housing 602 and is moveable, e.g. translatable, relative to the housing 602. The first adjustable member 604a includes at least one fixation aperture 606a configured to receive a fixation element therein to affix the first adjustable member 604a to bone. The second adjustable member 604b includes at least one fixation aperture 606b configured to receive a fixation element therein to affix the second adjustable member 604b to bone. In this embodiment, the housing 602 may include no fixation apertures. The second adjustable member 604b is at least partially disposed within the housing 602 and is moveable, e.g., translatable, relative to the housing 602. The first and second adjustable members 604a, 604b are positioned on opposing sides of the housing 602 relative to one another. That is, the second adjustable member 604b is positioned at least partially within an opposite end of the housing 602 relative to the first adjustable member 604a. The housing 602 includes two separate cavities 631a, 631b for receiving a respective adjustable member 604a, 604b therein. The adjustable implant 600 includes a first actuation assembly 616a configured to move the first adjustable member 604a relative to the housing 602, and a second actuation assembly 616b configured to move the second adjustable member 604b relative to the housing 602, such that each adjustable member 604a, 604b is individually controlled by its respective actuation assembly 616a, 616b. In this embodiment, the actuation assemblies 616a, 616b are substantially similar to the actuation assembly 116 of FIGS. 8-13. That is, the actuation assemblies 616a, 616b can each include an actuator 118 configured to be activated by an external adjustment device 400 (FIGS. 42-44), a gear assembly 120 coupled to the actuator 118, a roller driver 312 coupled with the gear assembly 120, at least one threaded roller 314 positioned radially about and threadingly engaged with the roller driver 312, and a cage 316 substantially surrounding the roller driver 312. The adjustable implant 600 also includes a first anti-jam feature 630a and a second anti-jam feature 630b positioned within respective cavities 631a, 631b. The anti-jam features 630a, 630b are identical to the anti-jam feature 130 (FIGS. 2, 5-6, and 8).

Figure 18:
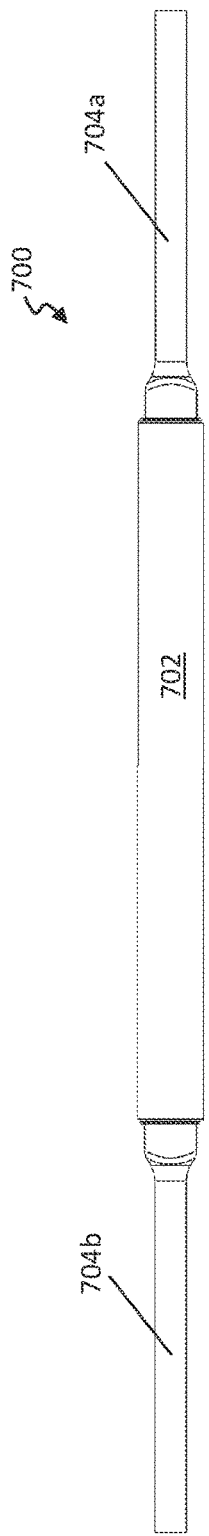
FIG. 18 shows a top view of an adjustable implant according to another embodiment of the disclosure.
Figure 19:
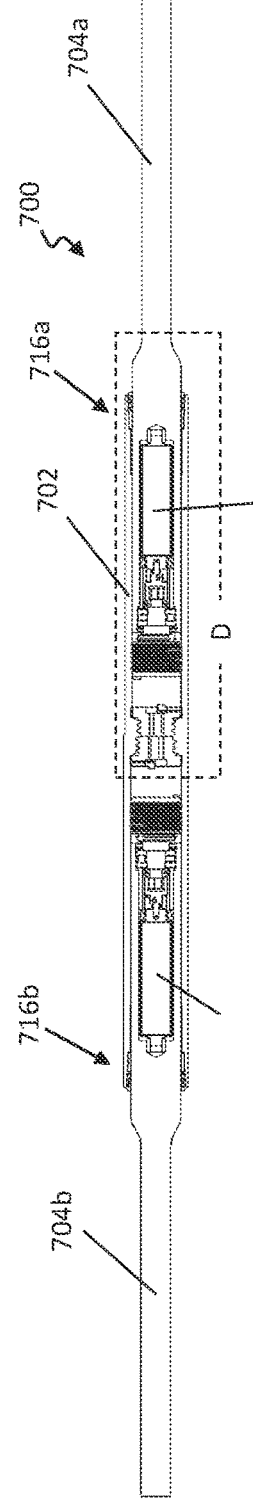
FIG. 19 shows a cross-sectional view of the adjustable implant of FIG. 18.
Figure 20:
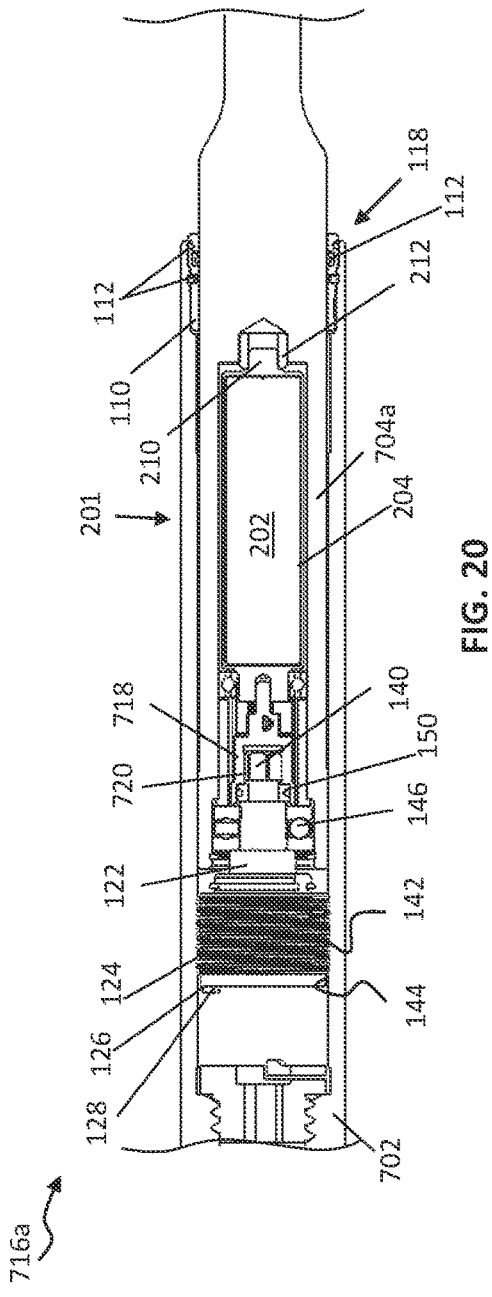
FIG. 20 shows an enlarged cross-sectional view of the adjustable implant taken at box D of FIG. 19.

FIGS. 18-20 show another embodiment of an adjustable implant 700 according to aspects of the disclosure. The adjustable implant 700 can be used as an adjustable spinal rod configured to be non-invasively actuated to adjust the curvature of a spine of a patient. The adjustable implant 700 is configured to be received in a plurality of pedicle screws positioned about the spine. As shown, the adjustable implant 700 includes a housing 702, a first adjustable member 704a and a second adjustable member 704b. The first adjustable member 704a is at least partially disposed within the housing 702 and is moveable, e.g. translatable, relative to the housing 702. The second adjustable member 704b is at least partially disposed within the housing 702 and is moveable, e.g., translatable, relative to the housing 702. The first and second adjustable members 704a, 704b are positioned on opposing sides of the housing 702 relative to one another. That is, the second adjustable member 704b is positioned within an opposite end of the housing 702 relative to the first adjustable member 704a. The housing 702 includes two separate cavities 731a, 731b for receiving a respective adjustable member 704a, 704b therein. The adjustable implant 700 includes a first actuation assembly 716a configured to move the first adjustable member 704a relative to the housing 702, and a second actuation assembly 716b configured to move the second adjustable member 704b relative to the housing 702, such that each adjustable member 704a, 704b is individually controlled by its respective actuation assembly 716a, 716b.

Details of the actuation assembly 716a are shown in FIG. 20. It is to be understood that while the discussion of FIG. 20 is relative to the actuation assembly 716a, it is equally applicable to the actuation assembly 716b. The actuation assembly 716a is similar to that of actuation assembly 116 of FIGS. 2-3, and therefore, like numbering represents like features, the descriptions of which are not repeated herein for brevity. The actuation assembly 716a differs from previously described embodiments in that the output driver 122 is directly coupled to the actuator 118, i.e., the magnetic assembly 201. That is, the actuation assembly 716a includes an actuator 118 configured to be activated by an external adjustment device 400, an output driver 122 coupled to the actuator 118, and a nut 124 disposed at least partially surrounding the output driver 122. No gear assembly is included. In this embodiment, the magnet housing 204 includes an extension 718 having an opening 720 with a keyed internal surface similar to the opening 252 of the drive stage 250 (FIG. 3) such that the keyed portion 140 of the output driver 122 is received within the opening 720 and is directly coupled to the magnet housing 204. Therefore, as the magnetic assembly 201 rotates due to an externally applied magnetic field, the output driver 122 also rotates in a 1:1 ratio. In another embodiment (not shown), an inverted roller screw 310 may be used in place of the output driver 122 and nut 124 in the actuation assemblies 716a, 716b.

With reference to FIGS. 21-41, an adjustable implant 300 is provided which includes a lock mechanism, which may be configured to lock and unlock rotation of a driver.

With reference to FIGS. 21-30, the lock mechanism 800 may be configured to allow the driver, e.g. the magnetic assembly 201, to drive in either forward or reverse, i.e., to rotate in either direction depending on the desired distraction or compression application, in response to rotation of the driver. Thus, in the unlocked position, the lock mechanism 800 permits the driver and the driven gear system 120 to rotate in either a clockwise direction or a counterclockwise direction as actuated by the driver. However, in the locked position, the lock mechanism 800 resists, and in some embodiments prevents entirely, any rotation in the absence of rotation of the driver. As a result, when in the locked position, the lock mechanism 800 resists, reduces, minimizes, or prevents back-driving and distraction loss caused by loads on the load side. The lock mechanism 800 may be used in combination with an output driver 122 and nut 124 as shown in implants 100, 500, and 700, with the inverted roller screw 310 as shown in implants 200 and 600, or with a lead screw 222 as shown in implant 300. Each of the foregoing torque receiving components includes a keyed feature 140, 326 which may be configured to engage the drive stage 250 as shown in, e.g. FIG. 21.

Figures 21, 22:
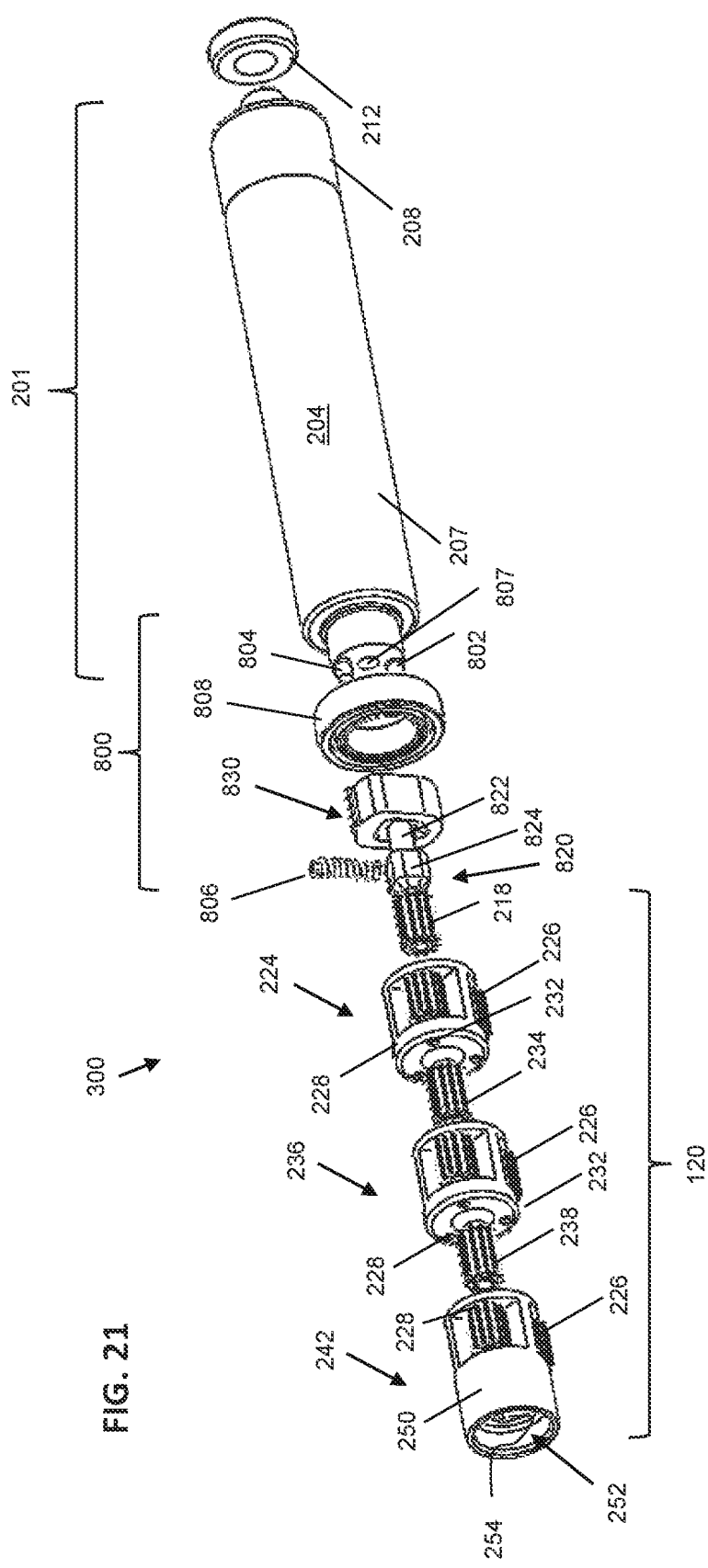
FIG. 21 shows an exploded perspective view of a gear assembly, a magnet assembly, and a magnet lock mechanism in accordance with an embodiment of the disclosure.
FIG. 22 shows an enlarged perspective view of the magnet housing of FIG. 21, in accordance with an embodiment of the disclosure.

The implant 300 includes a driver, which may be any actuator of rotational motion. In the embodiment depicted in FIG. 21, the driver is a magnetic assembly 201 as described previously herein, including a cylindrical permanent magnet 202 that is configured to be rotated by the application of a magnetic field, and a magnet housing 204 disposed about the cylindrical permanent magnet 202. The magnet housing 204 may be made up of separate magnet cups 207, 208 as shown in FIG. 21. However, in other embodiments, the driver may be, e.g., a motor. Further, in various embodiments, the driven gear system may be a gear assembly 120 as described herein, and may particularly be a planetary gear system including a sun gear 218 that is configured to engage a ring gear 246 (see FIGS. 28-30, 32, 40, 41) via a plurality of planetary gears 226 (see FIG. 21). However, in other embodiments, the driven gear assembly may be, for example, a cycloid gear assembly. In still other embodiments, the magnetic assembly 201 may engage the lead screw, output driver, or inverted roller screw directly, in the manner of implant 700 (FIGS. 18-20), without a driven gear assembly interposed between the magnetic assembly 201 and the lead screw, output driver, or inverted roller screw.

As noted, FIGS. 21-22 illustrate an embodiment in which the driver is in the form of a magnetic assembly 201 including a cylindrical permanent magnet 202 disposed within a magnet housing 204. The magnet housing 204 includes a first drive pin 802 and a second drive pin 804. As best shown in FIG. 22, each of the first and second drive pins 802, 804 extends axially from a first end of the magnet housing 204, in a direction parallel to a longitudinal axis of the cylindrical magnet 202 and magnet housing 204. The first and second drive pins 802, 804 may be arranged on the end face of the magnet housing 204 such that they are disposed substantially opposite one another, spaced about 180 degrees apart from one another on the end face of the magnet housing 204. The magnet housing 204 may further include a central recess 807 that is open to the first end of the magnet housing 204, and is disposed between the first drive pin 802 and the second drive pin 804. The central recess 807 may be centered on, or concentric with the longitudinal, i.e. rotational axis of the cylindrical magnet 202 and the magnet housing 204.

Referring back to FIG. 21, a keyed drive gear 820 is configured to be driven by the driver, e.g., by magnet housing 204, via the keeper 830, discussed further herein. The keyed drive gear 820, shown in detail in FIGS. 26-27, includes a central pin 822 coupled to a keyed portion 824, and a gear 218 coupled to the keyed portion 824 at an end opposite the end at which the keyed portion 824 is coupled to the central pin 822. Thus, the keyed portion 824 is disposed between the central pin 822 and the gear 218, each of which is coupled to the keyed portion 824 of the drive gear 820 at opposing ends thereof. The central pin 822, the keyed portion 824, and the gear 218 may be substantially coaxial with one another. As noted above, the gear 218 may be a sun gear in a planetary gear system. When assembled, the central pin 822 is configured to be disposed at least partly within the central recess 807 of the magnet housing 204 (see, e.g., FIGS. 21-22). The keyed portion 824 may have any non-circular keyed cross-sectional geometry configured to transfer torque such as, for example, square, hexagon, rectangle, star, etc. In particular embodiments, the keyed portion 824 may have a square cross-sectional geometry.

A keeper 830 is disposed over at least a portion of the drive gear 820, and is interposed between the drive gear 820 and the driver. The keeper 830 is configured to move, e.g. by rotating, from a locked position to an unlocked position in response to rotation of the driver, e.g., magnet housing 204. In the locked position, the keeper 830 is configured to resist, reduce, minimize, or in certain embodiments prevent rotation of the drive gear 820 and the magnet housing 204 under a load on the driven gear system 120, and in the unlocked position, the keeper 830 is configured to permit rotation of the drive gear 820 and the driver, e.g., magnet housing 204.

Figure 25:
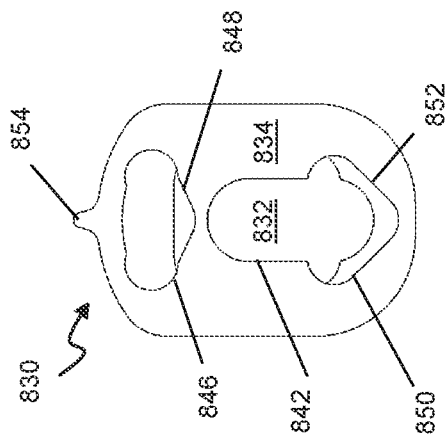
FIGS. 23, 24, and 25 show perspective, front, and back views, respectively, of a keeper as deployed in the lock mechanism of FIG. 21, in accordance with embodiments of the disclosure.
Figure 24:
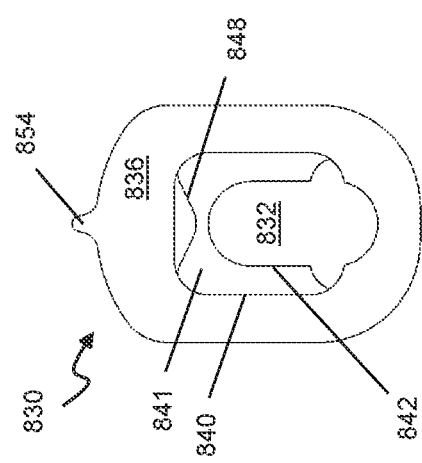
Figure 23:
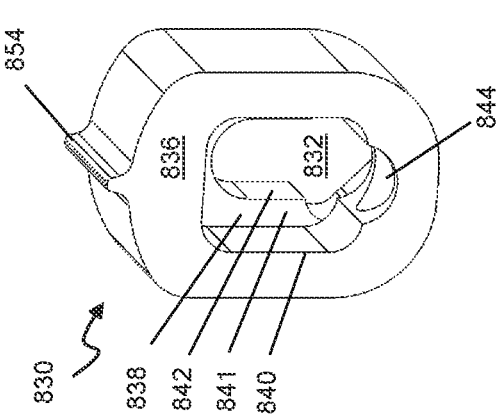
Figure 27:
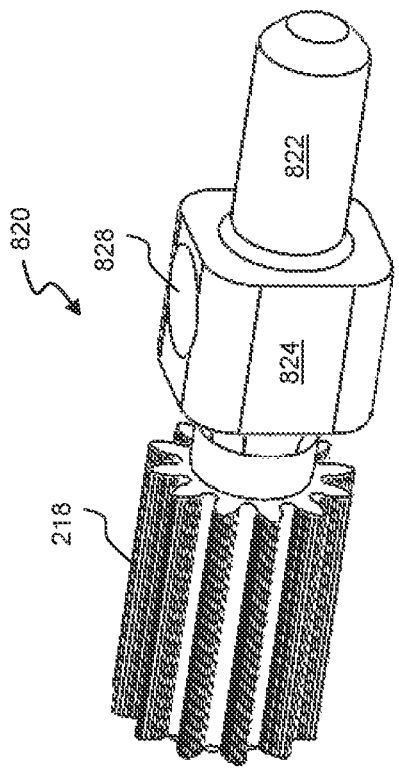
FIGS. 26-27 show perspective views of a keyed drive gear as deployed in the lock mechanism of FIG. 21, in accordance with embodiments of the disclosure.
Figure 26:
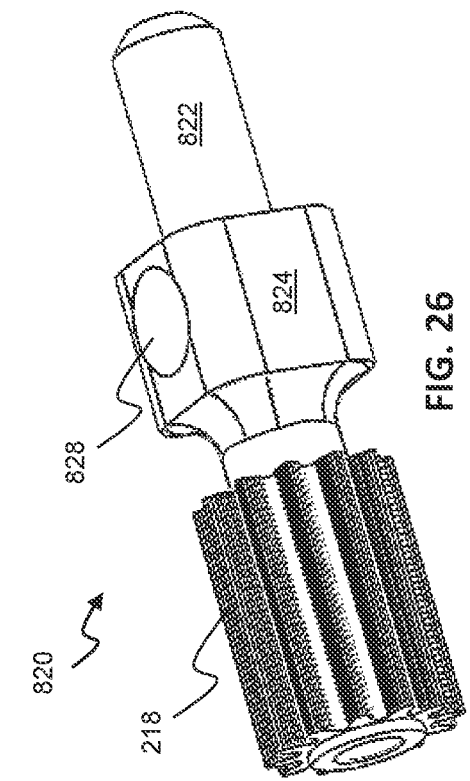

As best seen in FIGS. 23-25, the keeper 830 includes a body having a first face 834 and a second face 836, where the first face 834 is configured to engage the driver, e.g., the magnet housing 204, and the second face 836 is configured to engage the driven gear system via the keyed drive gear 820.

A keyed opening 841 is disposed within the body and is open to the second face 836. The keyed opening 841 is configured to receive and rotatably engage the keyed portion 824 of the drive gear 820. The keyed opening 841 may extend from the second face 836 of the body of keeper 830 through a partial thickness of the keeper 830. The keyed opening 841 is shaped and dimensioned to provide a complementary fit with the keyed portion 824 of the drive gear 820, such that, for example, the keyed portion 824 fits in male/female engagement within the keyed opening 841 of the keeper 830. Where, for example, the keyed portion 824 has a square, hexagon, rectangle, star, or other shape, the keyed opening 841 may have a corresponding square, hexagon, rectangle, star, or other shape that is dimensioned to receive the complementary square, hexagon, rectangle, star, or other keyed shape with a close fit. As a result, the keeper 830 and the drive gear 820 are rotationally fixed to one another via the keyed opening 841. For example, in embodiments in which the keyed portion 824 is square shaped, the keyed opening 841 may also be square shaped.

The keeper 830 may also include an opening 832 in the body, which is configured to receive the center pin 822 of the drive gear 820. The opening may extend from the first face 834 of the keeper 830 through at least a partial thickness of the body. The opening 832 and the keyed opening 841 may be fluidly coupled with one another, such that the opening 832 and the keyed opening 841 may partially overlap with one another. Therefore, the opening 832 may effectively extend from the first face 834 through a full thickness of the body of the keeper 830 to the second face 836 in certain areas. The keyed opening 841 may be bounded by drive surfaces 840, which are configured to drive rotation of the keyed portion 824 of the drive gear 820, while the opening 832 may be bounded by shaft relief surfaces 842, which are configured to permit translation of the center pin 822. In particular, the opening 832 may include an oblong or slot-shaped portion defined by the shaft relief surfaces 842, as shown in FIGS. 25, 29, and 30. This oblong shape may permit the body of the keeper 830 to translate relative to the center pin 822 in operation, as illustrated in the change in relative position of center pin 822 and opening 832 from the locked position of FIG. 29 to the unlocked position of FIG. 30. The keeper 830 may further include a stepped surface 838, shown in FIG. 23, disposed between the drive surfaces 840 and the shaft relief surfaces 842.

The keeper 830 further includes at least one lock tooth 854 disposed on a first end of the keeper 830, and extending axially therefrom. The lock tooth 854 is configured to releasably mesh with or engage the internal teeth 248 on the inner wall 244 of a ring gear 248 of the driven gear system in use (see FIGS. 29-30).

The keeper 830 may further include a first detent 846 disposed on the first face 834 of the keeper 830, the first detent 846 being configured to engage the first drive pin 802. The first detent 846 may particularly be disposed between the opening 832 and the first end of the body (which includes the lock tooth 854). The keeper 830 may further include a second detent 850, also disposed on the first face 834 of the keeper 830, the second detent 850 being configured to engage the second drive pin 804. The second detent 850 may particularly be disposed at the second end of the keeper 830, opposite the first end, and in fluid connection with the opening 832. It is noted that the first detent 846 may alternatively receive the second drive pin 804, and the second detent 850 may receive the first drive pin 802, to the same result.

Each of the first detent 846 and the second detent 850 may include a respective ramp surface 848, 852, along which the respective drive pin 802, 804 is configured to travel. The first ramp 848 and second ramp 852 may each be configured to be curved or angled, having approximately or substantially a u-shaped or v-shaped ramp surface. Each ramp 848, 852 may include a zenith which is laterally aligned with one another, and are also laterally aligned with the lock tooth 854 on the keeper 830. Accordingly, the drive pins 802, 804 disposed in each of the first detent 846 and the second detent 850 are disposed in the zeniths of the first ramp 848 and the second ramp 852 when the keeper 830 is in the locked position. The drive pins 802, 804 disposed in each of the respective first and second detents 846, 850 are configured to move up the respective first ramp 848 and the second ramp 852 when the keeper 830 moves into the unlocked position. In this manner, the first detent 846 and the second detent 850 are configured to permit rotation of the driver, e.g., magnet housing 204, relative to the keeper 830 to an extent limited by a length of the first ramp 848 and the second ramp 852. In certain embodiments, the first detent 846 and the second detent 850 each extend through a partial thickness of the keeper 830.

As illustrated in FIG. 23, the keeper 830 further includes a hole 844 extending from the keyed opening 841 through the second end of the keeper 830. The second end of the keeper 830 is the end opposite the first end, on which the lock tooth 854 is disposed. The keyed portion 824 of drive gear 820 also includes a hole 828 (see FIGS. 26-27) which, when assembled as in FIG. 28, is aligned with hole 844. Thus, the holes 844 and 828 in the keeper 830 and the keyed portion 824 of the drive gear 820 form a substantially continuous hole or channel. The lock mechanism 800 further includes a biaser 806 disposed within the aligned holes 844 and 828. The biaser 806 may be, for example, a spring. The biaser 806 may be configured to bias the keeper 830 across, or in a direction substantially perpendicular to a longitudinal axis of the magnet housing 204 and the drive gear 820. With reference to FIG. 21, the lock mechanism 800 may further include a radial bearing 808, which may be disposed about at least a portion of the magnet housing 204, the keeper 830, and the keyed drive gear 820, and may be configured to maintain a coaxial relationship between two or more of an end portion of the magnet housing 204, the keeper 830, and the keyed drive gear 820.

In operation, the lock mechanism 800 including the keeper 830, defaults to a locked position when the driver, e.g., magnet housing 204, is stationary (see FIG. 29). In the locked position, the biaser 806 is configured to bias the keeper 830 relative to the ring gear 246 and the drive gear 820, such that the lock tooth 854 on the keeper 830 is biased into meshed engagement with the teeth 248 on the inner surface 244 of the ring gear 246. In particular, the lock tooth 854 may be maintained in engagement between two teeth 248 of the ring gear 246 under the biasing force of biaser 806 in its expanded condition. This biasing force may be applied across or perpendicular to the longitudinal axis of the magnet housing 204 and the keyed drive gear 820. Due to the geometry of the detents, the first and second drive pins 802, 804 are disposed in the zenith positions of each of the respective ramps 848, 852 in the locked position. In this position, the keeper 830 resists rotation of the drive gear 820 and the magnet housing 204. This resistance to rotation is independent of any load on the driven gear system.

Upon, and in response to rotation of the driver, e.g., the magnet housing 204, the keeper 830 transitions from the locked position to the unlocked position. As the magnet housing 204 rotates, either in a clockwise or counterclockwise direction, the drive pins 802, 804 move out of the zenith position following the curve or slope of ramps 848, 852. In the embodiment shown in FIG. 30, the magnet housing 204 has rotated in a counter-clockwise direction, although the keeper 830 would function analogously if the rotation were clockwise. This rotation causes the keeper 830 to translate axially relative to the center pin 822 in the direction of the second end, opposite the first end, urged by the interaction between the ramps 848, 852 and the drive pins 802, 804. Relative to the translation of the keeper 830 toward the unlocked position, the lock tooth 854 is disposed on a trailing end of the keeper 830. This translation of the keeper 830 compresses the biaser 806 (FIG. 28), and causes the lock tooth 854 to disengage from the ring gear 246. With the lock tooth 854 now disengaged from the teeth 248 of the ring gear 246, the keeper 830 moves to its unlocked position, in which the keyed drive gear 820, and therefore the magnet housing 204 and the driven gear assembly 120, are free to rotate relative to the ring gear 246.

Upon, and in response to a cessation of rotation of the magnet housing 204, the opposite process occurs. In the absence of rotation of the magnet housing 204, and under the biasing force of biaser 806, the drive pins 802, 804 move downward along the ramps 848, 852 to return to the zenith position depicted in FIG. 29, and the keeper 830 translates axially relative to the central pin 822. The lock tooth 854 is on the leading end of the keeper 830 with respect to this translation motion toward the locked position. Lock tooth 854 engages the teeth 248 of the ring gear 246, thereby preventing rotation of the keeper 830, and therefore the keyed drive gear 820, which is rotationally fixed to the keeper 830. When the keyed drive gear 820 is rotationally locked, so too are the sun gear 218, the balance of gear assembly 120, and the lead screw 222 or other torque receiving component or element. In this manner, regardless or independently of the load placed on the lead screw 222 and the gear assembly 120, distraction or compression loss is resisted, and may in some embodiments be prevented.

With reference to FIGS. 31-41, the adjustable implant 300 may include a lock mechanism 900, which may provide an alternative embodiment to the implants 300 including the lock mechanism 800 described previously. Like the lock mechanism 800, the lock mechanism 900 is configured to lock and unlock rotation of a driver and a lead screw 222 or other torque receiving feature or component such as, e.g., an output driver 122 and nut 124 as illustrated in the context of adjustable implants 100, 500, and 700, or an inverted roller screw 310 as illustrated in the context of adjustable implants 200 and 600.

Like the lock mechanism 800, the lock mechanism 900 may be configured to allow the driver to drive in either forward or reverse, i.e., to rotate in either clockwise or counterclockwise direction depending on the desired distraction or compression application, in response to rotation of the driver. Thus, in the unlocked position, the lock mechanism 900 permits the driver and the lead screw to rotate in either a clockwise direction or a counterclockwise direction as actuated by the driver. However, in the locked position, the lock mechanism 900 resists, and in some embodiments prevents entirely, any rotation in the absence of rotation of the driver. As a result, the lock mechanism 900 resists, reduces, minimizes, or prevents distraction loss caused by loads on the lead screw 222 when in the locked position.

In various embodiments, the driver may be any actuator of rotational motion. For example, in the embodiment depicted in FIGS. 31-41, the driver is a magnetic assembly 201 as described herein, including a cylindrical permanent magnet 202 that is configured to be rotated by the application of a magnetic field. A magnet housing 204 may be disposed about the cylindrical permanent magnet 202. The magnet housing 204 may be made up of separate magnet cups 207, 208 as shown in FIG. 32. In other embodiments, the driver may be, e.g., a motor.

As noted, FIGS. 32-33 illustrate an embodiment in which the driver is in the form of a cylindrical permanent magnet 202 (FIG. 39) disposed within a magnet housing 204. The magnet housing 204 includes a first drive pin 902 and a second drive pin 904. As best shown in FIG. 33, each of the first and second drive pins 902, 904 extends axially from a first end of the magnet housing 204, in a direction parallel to the axis of rotation of the cylindrical permanent magnet 202. The first and second drive pins 902, 904 may be arranged such that they are disposed substantially opposite one another, spaced about 180 degrees apart from one another on the end face of the magnet housing 204.

Figure 38:
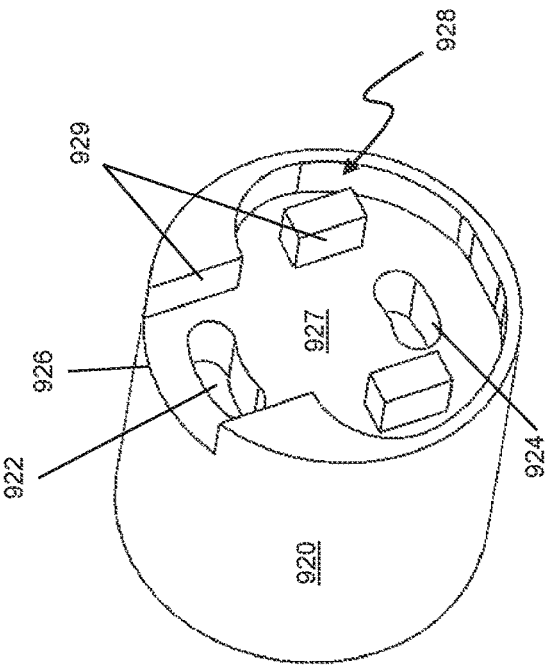
FIGS. 37-38 show perspective views of a keyed drive output as deployed in the lock mechanism of at least FIG. 32, in accordance with embodiments of the disclosure.
Figure 37:
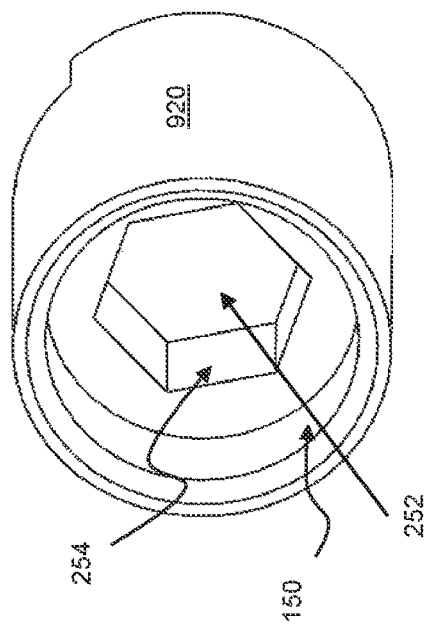

A keyed drive stage 920, shown in detail in FIGS. 37-38 and in context in FIGS. 31, 32, and 39-41, is configured to be driven by the driver, e.g., by the magnet housing 204. The keyed drive stage 920 includes, on a torque input end (best seen in FIG. 38), a first rotational slot 922 and a second rotational slot 924, each configured to receive one of the first and second drive pins 902, 904. As such, first and second rotational slots 922 and 924 may be arranged such that they are disposed substantially opposite one another, spaced about 180 degrees apart from one another on the input end of the keyed drive stage 920. Each of the first and second rotational slots 922 and 924 may have an arcuate shape, configured to allow a limited amount of rotation of the driver relative to the rotational slots 922, 924. The input end may further include a recess 927 shaped and dimensioned to receive a keeper 930 as described herein, and to allow the keeper 930 to translate across a rotational axis of the keyed drive stage 920 as further described herein. Still further, the recess 927 may include vertical guide surfaces 929 configured to define or guide the keeper 930 on the translational path of the keeper 930. The recess 927 may further be configured to allow the keeper 930 to translate beyond or across the outer circumference of the end of the keyed drive stage 920, to allow the keeper 930 to engage with a ring gear 246 disposed about the keyed drive stage 920, as described further herein.

On the second, torque output end of the keyed drive stage 920 (best seen in FIG. 37), an opening 252 having a keyed internal surface 254 is provided, as described elsewhere herein. The opening 252 may be configured to matingly receive and engage a keyed male feature such as, e.g., an external keyed surface 140 on the end of a lead screw 222, to transmit torque. Alternatively, an external keyed surface 140 on the end of an output driver 122 or an external keyed surface 326 on the end of an inverted roller screw 310 may similarly engage the opening 252 in the keyed drive stage 920. The keyed opening 252 may have any cross-sectional geometry configured to transmit torque, for example, square, rectangle, hexagon, or star. The keyed drive stage 920 may further include a retainer 150 as described herein relative to, e.g., FIGS. 3, 9, 20, 31, and 39.

Figure 36:
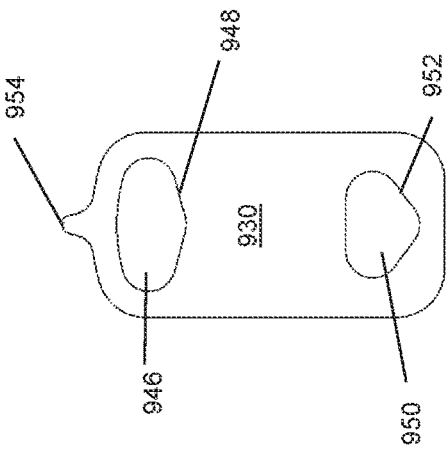
FIGS. 34, 35, and 36 show perspective, front, and back views, respectively, of a keeper as deployed in the lock mechanism of FIG. 32, in accordance with embodiments of the disclosure.
Figure 35:
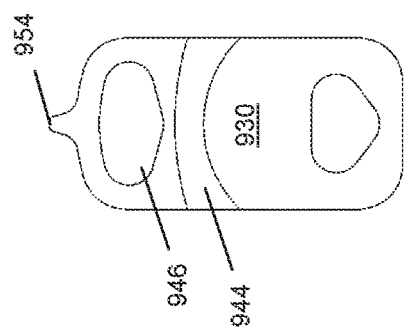
Figure 34:
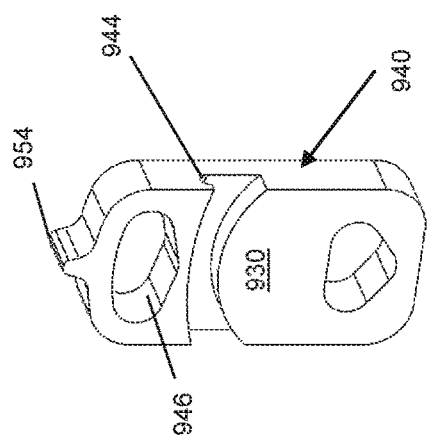

A keeper 930, shown in detail in FIGS. 34-36, and in context in FIGS. 31, 32, and 39-41, may be configured to be disposed within the recess 927 in the keyed drive stage 920. The keeper 930 is configured to move from a locked position to an unlocked position in response to rotation of the driver, e.g., magnet housing 204. In particular, the keeper 930 is configured to rotate and to translate in response to the rotation of the driver, thereby moving from the locked position to the unlocked position. In the locked position, the keeper 930 is configured to resist, reduce, minimize, or in certain embodiments prevent rotation of the keyed drive stage 920 and the magnet housing 204 under a load on the lead screw 222. In the unlocked position, the keeper 930 is configured to permit rotation of the keyed drive stage 920 and the driver, e.g., magnet housing 204.

As best seen in FIGS. 34-36, the keeper 930 includes a body configured to be received within the recess 927 (FIG. 38) in the keyed drive stage 920. The keeper 930 may include drive surfaces 940 which are configured to cooperate with the vertical guide surfaces 929 on the recess 927 to allow the keeper 930 to translate along the recess 927, and to allow the keeper 930 to drive rotation of the keyed drive stage 920. The drive surfaces 940 may be straight or substantially straight surfaces that are parallel or substantially parallel to one another, and perpendicular to the axis of rotation of the keyed drive stage 920.

The keeper 930 may include at least one lock tooth 954 disposed on a first end of the keeper 930, and extending axially therefrom. The lock tooth 954 is configured to releasably mesh with or engage the internal teeth 248 on the inner wall 244 of a ring gear 248 in use (see FIGS. 40-41). The lock tooth may be any mating male/female shape, for example square or triangular tooth shapes. The keeper 930 further includes a first detent 946, which may be disposed at the first end, near the lock tooth 954, and may be laterally aligned with the lock tooth 954. The first detent 946 may be configured to engage the first drive pin 902 in use. The keeper 930 may further include a second detent 950, disposed at the second end of the keeper 930 opposite the first end, the second detent 950 being configured to engage the second drive pin 904. The second detent may also be laterally aligned with the first detent 946 and the lock tooth 954. It is noted that the first detent 946 may alternatively engage the second drive pin 904, and the second detent 950 may engage the first drive pin to equal effect.

Each of the first detent 946 and the second detent 950 may include a respective ramp surface 948, 952, along which the respective drive pin 902, 904 is configured to travel. The first ramp 948 and second ramp 952 may each be configured to be curved or angled, similar to first ramp 848 and second ramp 852 on keeper 830 (see FIG. 25), having an approximately or substantially u-shaped or v-shaped ramp surface. Each ramp 948, 952 may include a zenith which is laterally aligned with the other, and also laterally aligned with the lock tooth 954 on the keeper 930. Accordingly, the drive pins 902, 904 disposed in each of the first detent 946 and the second detent 950 are disposed in the zeniths of the first ramp 948 and the second ramp 952 and in line with the lock tooth 954 when the keeper 930 is in the locked position. The drive pins 902, 904 disposed in each of the respective first and second detents 946, 950 are configured to move up the respective first ramp 948 and the second ramp 952 when the keeper 930 moves into the unlocked position. In certain embodiments, the first detent 946 and the second detent 950 each extend through a full thickness of the keeper 930.

As shown in FIGS. 34-36, the keeper 930 further includes a spring guide slot 944. Unlike the detents 946 and 950, the spring guide slot 944 may extend through only a partial thickness of the keeper 930. The spring guide slot 944 may be curved, and may be configured to receive a portion of a biaser or spring 906 (see FIG. 32) therein. As such, the shape and size of the spring guide slot 944 may be complementary to that of a portion of the spring 906.

The lock mechanism 900 further includes the biaser or spring 906, which may be disposed partially within the spring guide slot 944, and partially within a spring contour 928 in the recess 927. The biaser 906 may be configured to bias the keeper 930 away from the spring contour 928. The recess 927 may be open at the end 926 that is opposite the spring contour 928. Thus, the biaser may be configured to bias the keeper 930 across, or in a direction substantially perpendicular to the rotational axis of the magnet assembly, such that the lock tooth 954 extends beyond the outer circumference of the keyed drive stage 920. In use, this allows the lock mechanism 900 to achieve the locked position shown in FIG. 40.

Figure 31:
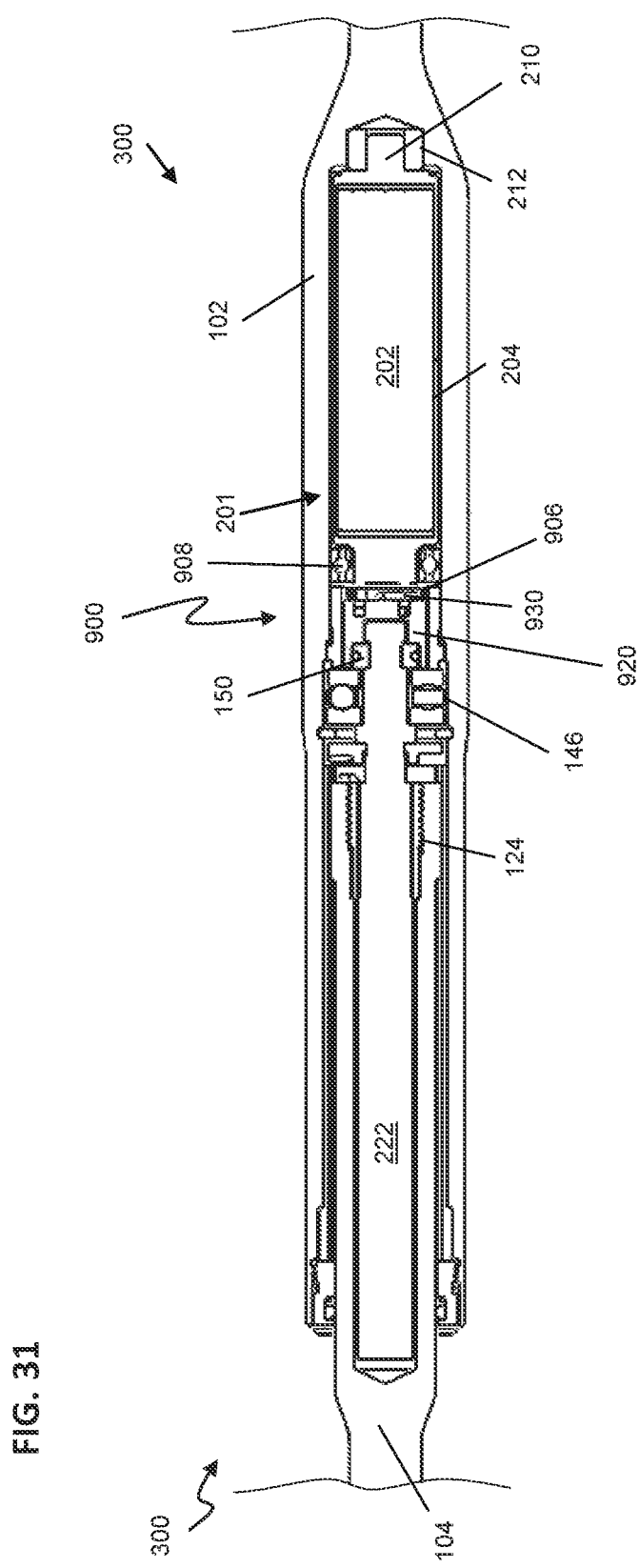
FIG. 31 shows a cross sectional view of a portion of an exemplary distraction and compression device including a lock mechanism in accordance with an embodiment of the disclosure.

With reference to FIGS. 31, 32 and 39, the lock mechanism 900 may further include a radial bearing 908, which may be disposed about at least a portion of the magnet housing 204, and may be configured to assist in maintaining the spatial relationships between the magnet housing 204, the keeper 930, and the keyed drive stage 920.

In operation, the lock mechanism 900 including the keeper 930, defaults to a locked position when the driver, e.g., magnet housing 204, is stationary (see FIG. 40). In the locked position, the biaser 906 is configured to bias the keeper 930 toward the open end 926 and against the spring contour 928 of the recess 927. Under the force of the biaser 906 in its expanded condition, the keeper 930 translates across the rotational axis toward and at least partially through the open end 926 of the recess 927, such that the lock tooth 954 on the keeper 930 extends beyond an outer circumference of the keyed drive stage 920 and is biased into meshed engagement with the teeth 248 on the inner surface 244 of the ring gear 246. Due to the geometry of the first and second detents 946, 950, the first and second drive pins 902, 904 are disposed in the zenith positions of each of the respective ramps 948, 952. In this position, the keeper 930 resists rotation of the keyed drive stage 920 and under a load on the lead screw 222 (see FIG. 39).

Upon, and in response to rotation of the driver, e.g., the magnet housing 204, the keeper 930 transitions from the locked position to the unlocked position. As the magnet housing 204 rotates, either in a clockwise or counterclockwise direction, the drive pins 902, 904 move out of the zenith position following the curve or slope of ramps 948, 952. In the position shown in FIG. 41, the magnet housing 204 has rotated in a counter clockwise direction, although the keeper 930 would function analogously if the rotation were clockwise. This rotation causes the keeper 930 to translate axially relative to the recess 927 in the direction away from the open end 926. Relative to this translation motion, the lock tooth 954 is disposed on a trailing end of the keeper 930. This translation causes the lock tooth 954 to disengage from the ring gear 246, and the biaser 906 to be compressed by the keeper 930, and in particular by spring guide slot 944. With the lock tooth 954 now disengaged from the teeth 248 of the ring gear 246, the keeper 930 moves to its unlocked position, in which the keyed drive stage 920, and therefore the lead screw 222, are free to rotate relative to the ring gear 246.

Upon, and in response to a cessation of rotation of the magnet housing 204, the opposite process occurs. In the absence of rotation of the magnet housing 204, and under the biasing force of biaser 906, the drive pins 902, 904 move downward along the ramps 948, 952 to return to the zenith position depicted in FIG. 40, and the keeper 930 translates axially relative to the recess 927. The lock tooth 954 is on the leading end of the keeper 930 with respect to this translation motion. Lock tooth 954 engages the teeth 248 of the ring gear 246, thereby preventing rotation of the keyed drive stage 920. Where the keyed drive stage 920 is rotationally fixed, so too is the lead screw 222. In this manner, regardless or independently of the load placed on the lead screw 222 or other torque receiving component or feature, back-driving and resulting distraction or compression loss are resisted, and may in some embodiments be prevented.

FIGS. 42-44 illustrate an external adjustment device 400 configured for applying a moving magnetic field to allow for non-invasive adjustment of the adjustable implant 100, 200, 300, 500, 600, 700 by turning a permanent magnet 202 within the adjustable implant 100, 200, 300, 500, 600, 700, as described. FIG. 42 illustrates the internal components of the external adjustment device 400, and for clear reference, shows the permanent magnet 202 of the adjustable implant 100, 200, 300, 500, 600, 700, without the rest of the assembly. The internal working components of the external adjustment device 400 may, in certain embodiments, be similar to that described in U.S. Patent Application Publication No. 2012/0004494, which is incorporated by reference herein. A motor 402 with a gear box 404 outputs to a motor gear 406. Motor gear 406 engages and turns central (idler) gear 408, which has the appropriate number of teeth to turn first and second magnet gears 410, 412 at identical rotational speeds. First and second magnets 414, 416 turn in unison with first and second magnet gears 410, 412, respectively. Each magnet 414, 416 is held within a respective magnet cup 418 (shown partially). An exemplary rotational speed is 60 RPM or less. This speed range may be desired in order to limit the amount of current density induced in the body tissue and fluids, to meet international guidelines or standards. As seen in FIG. 42, the south pole 422 of the first magnet 414 is oriented the same as the north pole 424 of the second magnet 416, and likewise, the first magnet 414 has its north pole 426 oriented the same as the south pole 428 of the second magnet 416. As these two magnets 414, 416 turn synchronously together, they apply a complementary and additive moving magnetic field to the radially-poled, permanent magnet 202, having a north pole 432 and a south pole 434. Magnets having multiple north poles (for example, two) and multiple south poles (for example, two) are also contemplated in each of the devices. As the two magnets 414, 416 turn in a first rotational direction 442 (e.g., counter-clockwise), the magnetic coupling causes the permanent magnet 202 to turn in a second, opposite rotational direction 444 (e.g., clockwise). The rotational direction of the motor 402 and corresponding rotational direction of the magnets 414, 416 is controlled by buttons 446, 448. One or more circuit boards 452 contain control circuitry for both sensing rotation of the magnets 414, 416 and controlling the rotation of the magnets 414, 416.

FIGS. 43 and 44 show the external adjustment device 400 for use with an adjustable implant 100, 200, 300, 500, 600 placed in the femur (FIG. 43) or the tibia (FIG. 44) or an adjustable implant 700 placed along a spinal curvature. The external adjustment device 400 has a first handle 454 for carrying or for steadying the external adjustment device 400, for example, steadying it against an upper leg 456 (as in FIG. 43) or lower leg 457 as in (FIG. 44). An adjustable handle 458 is rotationally attached to the external adjustment device 400 at pivot points 460, 462. Pivot points 460, 462 have easily lockable/unlockable mechanisms, such as a spring-loaded brake, ratchet, or tightening screw, so that a desired angulation of the adjustable handle 458 in relation to the housing 464 can be adjusted and locked in orientation. The adjustable handle 458 is shown in two different positions in FIGS. 43 and 44. In FIG. 43, the adjustable handle 458 is set so that the apex 466 of the loop 468 rests against the housing 464. In this position, the patient 470 is able to hold onto one or both of the grips 472, 474 while the adjustment procedure (for example transporting bone between 0.10 mm to 1.50 mm) is taking place. It is contemplated that the procedure could also be a lengthening procedure for a bone lengthening device or a lengthening procedure for a lengthening plate which is attached external to the bone. Turning to FIG. 44, when the adjustable implant 100, 200, 300, 500, 600 is implanted in a tibia, the adjustable handle 458 may be changed to a position in which the patient 470 can grip onto the apex 466 so that the magnet area 476 of the external adjustment device 400 is held over the portion the adjustable implant 100, 200, 300, 500, 600 containing the permanent magnet 202. In both cases, the patient 470 is able to clearly view the control panel 478 including a display 482. In a different configuration from the two directional buttons 414, 416 in FIG. 42, the control panel 478 includes a start button 484, a stop button 486 and a mode button 488. Control circuitry contained on circuit boards 452 may be used by the surgeon to store important information related to the specific aspects of each particular patient. For example, in some patients an implant may be placed antegrade into the tibia. In other patients the implant may be placed either antegrade or retrograde about the femur. In still other patients, the implant may be placed about an area of curvature in the spine of the patient. In each of these cases, it may be desired to move the bone either from distal to proximal or from proximal to distal. By having the ability to store information of this sort that is specific to each particular patient within the external adjustment device 400, the external adjustment device 400 can be configured to direct the magnets 414, 416 to turn in the correct direction automatically, while the patient need only place the external adjustment device 400 at the desired position, and push the start button 484. The information of the maximum allowable bone transport length per day and maximum allowable bone transport length per session can also be input and stored by the surgeon for safety purposes. These may also be added via an SD card or USB device, or by wireless input. An additional feature is a camera at the portion of the external adjustment device 400 that is placed over the skin. For example, the camera may be located between first magnet 414 and second magnet 416. The skin directly over the implanted permanent magnet 202 may be marked with indelible ink. A live image from the camera is then displayed on the display 482 of the control panel 478, allowing the user to place the first and second magnets 414, 416 directly over the area marked on the skin. Crosshairs can be overlaid on the display 482 over the live image, allowing the user to align the mark on the skin between the crosshairs, and thus optimally place the external adjustment device 400.

Other external adjustment devices can be used to cause actuation of the distraction devices described herein. Such external adjustment devices include, for example, those described in U.S. Pat. No. 8,382,756, published on Feb. 26, 2013; U.S. Pat. No. 9,248,043, published on Feb. 2, 2016; U.S. Pat. No. 9,078,711, published on Jul. 14, 2015; U.S. Pat. No. 9,044,281, published on Jun. 2, 2015; U.S. Pat. No. 11,246,694, published on Feb. 15, 2022; U.S. Pat. App. Pub. No. 2016/0113683 A1, published on Apr. 28, 2016; U.S. Pat. No. 10,835,290, published on Nov. 17, 2020; and International Patent App. No. PCT/US2020/017338, published as WO 2020/163800 A1 on Aug. 13, 2020, all of which are incorporated herein by reference as if set forth in their entirety.

While implementations above are primarily in the context of externally magnetically driven systems, other drive systems can be used. For example, in addition to or instead of the magnet-based driving, one or more of the drive elements can take the form of an implanted electric motor. The implanted electric motor can be powered by an external power source (e.g., via a radiofrequency link, via an ultrasonic energy transfer technique, via an inductive connection, via another technique, or via combinations thereof) or an implanted power source (e.g., a battery, which may be charged by the external power source). The implanted power source may be within the implant (e.g., within a housing thereof) or separate from the implant and coupled to the implant via a cable.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on,"

above and in the claims is intended to mean, "based at least in part on," such that an unrecited feature or element is also permissible.

The terminology used herein is for the purpose of describing particular embodiments only and is not intended to be limiting of the disclosure. As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups. As used herein, "substantially" refers to largely, for the most part, entirely specified or any slight deviation which provides the same technical benefits of the disclosure.

The implementations set forth in the foregoing description do not represent all implementations consistent with the subject matter described herein. Instead, they are merely some examples consistent with aspects related to the described subject matter. Although a few variations have been described in detail herein, other modifications or additions are possible. In particular, further features and/or variations can be provided in addition to those set forth herein. For example, the implementations described above can be directed to various combinations and sub-combinations of the disclosed features and/or combinations and sub-combinations of one or more features further to those disclosed herein. In addition, the logic flows depicted in the accompanying figures and/or described herein do not necessarily require the particular order shown, or sequential order, to achieve desirable results. The scope of the following claims may include other implementations or embodiments.

What is claimed is:

1. An adjustable implant comprising:
   a housing having an internal thread and defining a cavity within the housing;
   a first adjustable member at least partially positioned within the housing and moveable relative to the housing within the cavity; and
   a first actuation assembly positioned within the first adjustable member and configured to move the first adjustable member relative to the housing, the first actuation assembly including:
      an actuator configured to be activated by an external adjustment device;
      a gear assembly coupled to the actuator;
      an output driver coupled to the gear assembly; and
      a nut disposed at least partially surrounding the output driver and having an outer thread configured to communicate with the internal thread of the housing;
   an anti-rotation lock configured to move from a locked position to an unlocked position in response to actuation of the actuator;
   wherein, in the locked position, the anti-rotation lock is configured to resist rotation of the output driver, and in the unlocked position, permits rotation of the output driver.

2. The adjustable implant of claim 1,
   wherein the nut includes at least one flat interior surface configured to engage at least one complementary flat exterior surface of the output driver;
   wherein the output driver includes a keyed portion configured to engage a complementary keyed portion of the gear assembly;
   wherein the gear assembly includes at least one planetary gear; and
   wherein the adjustable implant further comprises a thrust bearing positioned about at least a portion of the output driver within the first adjustable member.

3. The adjustable implant of claim 1, further comprising:
   an intermediary member positioned between the housing and the adjustable member, the intermediary member including at least one groove facing an outer surface of the adjustable member and at least one groove facing an inner surface of the housing;
   a radial seal, o-ring or retainer positioned within the at least one groove facing the outer surface of the adjustable member; and
   a radial seal, o-ring or retainer positioned within the at least one groove facing the inner surface of the housing,
   wherein the adjustable member includes an oblong outer cross-section and the intermediary member includes an oblong inner cross-section.

4. The adjustable implant of claim 1, further comprising:
   an anti jam feature positioned within the cavity opposite the first adjustable member, wherein the anti jam feature includes a spring tab;
   wherein the output driver of the actuation assembly includes a complementary tab configured to engage the spring tab of the anti jam feature when the adjustable implant is in a fully retracted state; and
   wherein the spring tab is configured to provide a spring force upon the output driver when the adjustable implant is in the fully retracted state.

5. The adjustable implant of claim 1, further comprising:
   a second adjustable member at least partially disposed within the housing and moveable relative to the housing, wherein the second adjustable member is positioned within an opposite end of the housing relative to the first adjustable member.

6. The adjustable implant of claim 1, further comprising:
   a second adjustable member at least partially disposed within the housing and moveable relative to the housing; and
   a second actuation assembly within the second adjustable member configured to move the second adjustable member relative to the housing,
   wherein the second adjustable member is positioned within an opposite end of the housing relative to the first adjustable member.

7. The adjustable implant of claim 1, wherein the actuator includes a magnetic assembly configured to be rotated upon application of a rotating magnetic field.

8. The adjustable implant of claim 7, further comprising:
   a maintenance member positioned proximate the actuator and configured to maintain a position of the magnetic assembly in the absence of the rotating magnetic field.

9. The adjustable implant of claim 1, wherein the anti-rotation lock comprises:
   a body;
   a keyed opening in the body, the keyed opening being configured to receive a complementarily keyed portion of a drive gear, wherein the anti-rotation lock and the drive gear are rotationally fixed to one another;
   an opening in the body configured to receive a center pin of the drive gear, and further configured to permit the body to translate axially relative to the center pin; and a lock tooth disposed on a first end of the body, the lock tooth being configured to releasably mesh with teeth on a ring gear.

10. An adjustable implant comprising:
a housing defining a cavity;
a first adjustable member at least partially positioned within the housing and moveable relative to the housing within the cavity; and
a first actuation assembly positioned within the first adjustable member and configured to move the first adjustable member relative to the housing, wherein the first actuation assembly includes:
   an actuator configured to be activated by an external adjustment device;
   a gear assembly coupled to the actuator;
   a roller driver coupled with the gear assembly;
   at least one threaded roller positioned radially about and threadingly engaged with both the roller driver and an internal thread of the housing; and
a cage substantially surrounding the roller driver and defining at least one aperture configured to receive the at least one threaded roller therein
an anti jam feature positioned within the cavity opposite the first adjustable member,
wherein the anti-jam feature includes a spring tab and the cage of the actuation assembly includes a complementary tab, the tab of the cage configured to engage the spring tab of the anti-jam feature when the adjustable implant is in a fully retracted state; and
wherein the spring tab is configured to provide a spring force upon the cage when the adjustable implant is in the fully retracted state.

11. The adjustable implant of claim 10, wherein the at least one threaded roller includes four threaded rollers positioned about 90° apart about the roller driver; and
wherein the at least one aperture includes four apertures, each configured to receive a respective threaded roller therein.

12. The adjustable implant of claim 10,
wherein, upon actuation of the actuator by the external adjustment device, the roller driver is configured to rotate thereby causing the at least one threaded roller to rotate, and
wherein the at least one threaded roller is configured to interact with the internal thread of the housing to cause the first adjustable member to move relative to the housing.

13. The adjustable implant of claim 10,
wherein the roller driver includes a keyed portion configured to engage a complementary keyed portion of the gear assembly;
wherein the gear assembly includes at least one planetary gear; and
wherein the adjustable implant further includes a thrust bearing positioned about at least a portion of the roller driver within the first adjustable member.

14. The adjustable implant of claim 10, wherein the actuator includes a magnetic assembly configured to be rotated upon application of a rotating magnetic field.

15. The adjustable implant of claim 14, further comprising:
a maintenance member positioned proximate the actuator and configured to maintain a position of the magnetic assembly in the absence of the rotating magnetic field.

16. The adjustable implant of claim 10, further comprising:
an anti-rotation lock configured to move from a locked position to an unlocked position in response to actuation of the actuator;
wherein, in the locked position, the anti-rotation lock is configured to resist rotation of the roller driver, and in the unlocked position, permits rotation of the roller driver.

17. The adjustable implant of claim 16, wherein the anti-rotation lock comprises:
a body;
a keyed opening in the body, the keyed opening being configured to receive a complementarily keyed portion of a drive gear, wherein the anti-rotation lock and the drive gear are rotationally fixed to one another;
an opening in the body configured to receive a center pin of the drive gear, and further configured to permit the body to translate axially relative to the center pin; and
a lock tooth disposed on a first end of the body, the lock tooth being configured to releasably mesh with teeth on a ring gear.

* * * * *